(12) United States Patent
Gregg et al.

(10) Patent No.: US 11,643,886 B2
(45) Date of Patent: May 9, 2023

(54) GEOTECHNICAL RIG SYSTEMS AND METHODS

(71) Applicant: Gregg Drilling, LLC, Signal Hill, CA (US)

(72) Inventors: John Gregg, Signal Hill, CA (US); Matthew Schubert, Signal Hill, CA (US); Phillip Schubert, Signal Hill, CA (US)

(73) Assignee: Gregg Drilling LLC, Signal Hill, CA (US)

( * ) Notice: Subject to any disclaimer, the term of this patent is extended or adjusted under 35 U.S.C. 154(b) by 0 days.

(21) Appl. No.: 17/378,607

(22) Filed: Jul. 16, 2021

(65) Prior Publication Data
US 2022/0042894 A1  Feb. 10, 2022

Related U.S. Application Data

(60) Provisional application No. 63/052,898, filed on Jul. 16, 2020.

(51) Int. Cl.
*E21B 19/14* (2006.01)
*B63B 27/10* (2006.01)
(Continued)

(52) U.S. Cl.
CPC ............ *E21B 19/146* (2013.01); *B63B 27/10* (2013.01); *B63B 35/4413* (2013.01); *B63C 11/52* (2013.01); *B63G 8/001* (2013.01); *E21B 7/02* (2013.01); *E21B 15/02* (2013.01); *E21B 19/00* (2013.01); *E21B 19/002* (2013.01);
(Continued)

(58) Field of Classification Search
CPC ........ E21B 19/146; E21B 15/02; E21B 19/00; E21B 19/002; E21B 44/00; E21B 49/025; B63B 27/10; B63B 35/4413; B63C 11/52; B63G 8/001; B63G 2008/007; G01N 3/40; G01N 33/24
See application file for complete search history.

(56) References Cited

U.S. PATENT DOCUMENTS 5,439,066 A * 8/1995 Gipson ................. E21B 43/114
175/81
5,681,982 A * 10/1997 Stoll ........................ G01N 3/40
73/84

(Continued)

FOREIGN PATENT DOCUMENTS

CA  2272773 C * 10/2000 ............... E21B 1/00
EP  0 984 132 A2  3/2000
(Continued)

OTHER PUBLICATIONS

PCT International Search Report; International App. No.: PCT/US2021/041894; dated Oct. 12, 2021; pp. 1-5.

*Primary Examiner* — Ryan D Walsh

(57) ABSTRACT

This invention relates generally to geotechnical rig systems and methods. In one embodiment, a cone penetration testing system includes, but is not limited to, a frame; at least one rotatable reel; at least one movable roller; and at least one sensor, wherein the at least one movable roller is configured to adjust a bend radius of at least one tube coiled about the at least one rotatable reel based at least partly on data received from the at least one sensor.

19 Claims, 17 Drawing Sheets

(51) Int. Cl.
  *B63B 35/44* (2006.01)
  *B63C 11/52* (2006.01)
  *B63G 8/00* (2006.01)
  *E21B 15/02* (2006.01)
  *E21B 19/00* (2006.01)
  *E21B 49/02* (2006.01)
  *G01N 3/40* (2006.01)
  *G01N 33/24* (2006.01)
  *E21B 44/00* (2006.01)
  *E21B 7/02* (2006.01)
  *E21B 19/20* (2006.01)

(52) U.S. Cl.
  CPC .............. *E21B 19/20* (2013.01); *E21B 44/00* (2013.01); *E21B 49/025* (2013.01); *G01N 3/40* (2013.01); *G01N 33/24* (2013.01); *B63G 2008/007* (2013.01)

(56) References Cited

U.S. PATENT DOCUMENTS

| | | | | |
|---|---|---|---|---|
| 6,321,596 | B1* | 11/2001 | Newman | G01N 3/32 73/811 |
| 7,029,206 | B2* | 4/2006 | Stockstill | F16L 1/23 405/168.4 |
| 9,038,733 | B2 | 5/2015 | Wijning et al. | |
| 2002/0000332 | A1* | 1/2002 | Merecka | E21B 19/22 175/203 |
| 2003/0010505 | A1* | 1/2003 | Gipson | E21B 19/22 166/77.2 |
| 2003/0106714 | A1* | 6/2003 | Smith | E21B 19/22 114/244 |
| 2006/0000619 | A1* | 1/2006 | Borst | E21B 19/22 166/77.2 |
| 2006/0159524 | A1 | 7/2006 | Thompson | |
| 2007/0221386 | A1* | 9/2007 | Rock | E21B 33/072 166/380 |
| 2011/0203803 | A1* | 8/2011 | Zemlak | E21B 19/002 166/349 |
| 2011/0289994 | A1* | 12/2011 | Smith | E21B 19/00 72/369 |
| 2016/0369614 | A1* | 12/2016 | Turner | E21B 19/22 |
| 2018/0355686 | A1* | 12/2018 | Boggess | E21B 19/22 |
| 2021/0086249 | A1* | 3/2021 | Martin | B21D 26/041 |
| 2022/0018196 | A1* | 1/2022 | Gregg | B63B 35/4413 |

FOREIGN PATENT DOCUMENTS

| | | | | |
|---|---|---|---|---|
| GB | 0 312 006 A | | 10/1997 | |
| GB | 2431418 A | * | 4/2007 | ............ E21B 19/22 |
| GB | 2440808 A | * | 2/2008 | ............ E21B 41/04 |
| GB | 2531781 A | * | 5/2016 | ......... B63B 35/4413 |
| WO | WO 2003/083514 A1 | | 10/2003 | |
| WO | WO-2017105411 A | * | 6/2017 | ............ B63B 35/03 |
| WO | WO-2018132861 A1 | * | 7/2018 | ........... B65H 75/425 |
| WO | WO 2019/231383 A1 | | 12/2019 | |

* cited by examiner

GEOTECHNICAL RIG SYSTEMS AND METHODS

PRIORITY CLAIM

This application is a non-provisional patent application of U.S. provisional patent application 63/052,898 filed Jul. 16, 2020, titled Remotely Operated Unmanned Amphibious Geotechnical Drilling and Cone Penetration Testing (CPT) System (DOCKET GD-P-02).

This application claims the benefit of and/or priority to each of the foregoing patent applications and any and all parent, grandparent, and great-grandparent applications thereof. The foregoing patent applications are incorporated by reference in their entirety as if fully set forth herein.

FIELD OF THE INVENTION

This disclosure relates generally to geotechnical rig systems and methods.

BACKGROUND

Known methods for geotechnical investigation, sampling, or drilling include use of direct human to machine interaction on site. The present disclosure includes embodiments related to geotechnical rig systems and methods that overcome at least these deficiencies in the art, including embodiments that enable a range of geotechnical work to be carried out without the need for direct human interaction on site.

SUMMARY

Embodiments disclosed herein relate generally to geotechnical rig systems and methods. In one embodiment, a rig includes, but is not limited to, a frame configured to deploy a drill string; at least one docking base disposed on the frame; at least one carousel with one or more addressed slots to stow one or more components, the at least one carousel being releasably coupled to the at least one docking base; and at least one arm that is configured to controllably retrieve and/or position the one or more components. In another embodiment, a carousel includes, but is not limited to, one or more addressed slots to stow one or more components including at least: one or more drill casings, and one or more sample vessels, a funneled base configured to releasably couple to a docking station of a geotechnical rig; and a lift point configured for maneuvering the carousel. In a further embodiment, a vessel system for sampling includes, but is not limited to a vessel; a crane; a rig including at least: a frame, and at least one docking base disposed on the frame; a plurality of interchangeable carousels each with one or more addressed slots to stow one or more components and each being configured to exchangeably couple to the at least one docking base; and a shuttle that is configured to controllably retrieve and/or position the one or more components.

In one embodiment, a rig for cone penetration testing includes, but is not limited to, a frame; at least one cassette including at least one rotatable reel; at least one sensor; at least one movable roller; at least one drive system; and at least one tube having at least one cone penetration testing head, the at least one tube configured to be coiled about the at least one rotatable reel and extendably thrusted using the at least one drive system, wherein the at least one movable roller is configured to adjust a bend radius of the at least one tube based at least partly on data received from the at least one sensor. In a further embodiment, a cassette system for cone penetration testing includes, but is not limited to, at least one rotatable reel; at least one sensor; and at least one movable roller, wherein the at least one movable roller is configured to adjust a bend radius of at least one tube coiled about the at least one rotatable reel based at least partly on data received from the at least one sensor. In another embodiment, a cone penetration testing system includes, but is not limited to, a frame; at least one rotatable reel; at least one movable roller; and at least one sensor, wherein the at least one movable roller is configured to adjust a bend radius of at least one tube coiled about the at least one rotatable reel based at least partly on data received from the at least one sensor.

BRIEF DESCRIPTION OF THE DRAWINGS

Embodiments are described in detail below with reference to the following drawings.

DETAILED DESCRIPTION

This disclosure relates generally to geotechnical rig systems and methods. Certain embodiments are set forth in the following description and in FIGS. 1-17 to provide a thorough understanding of such embodiments.

Figure 1:
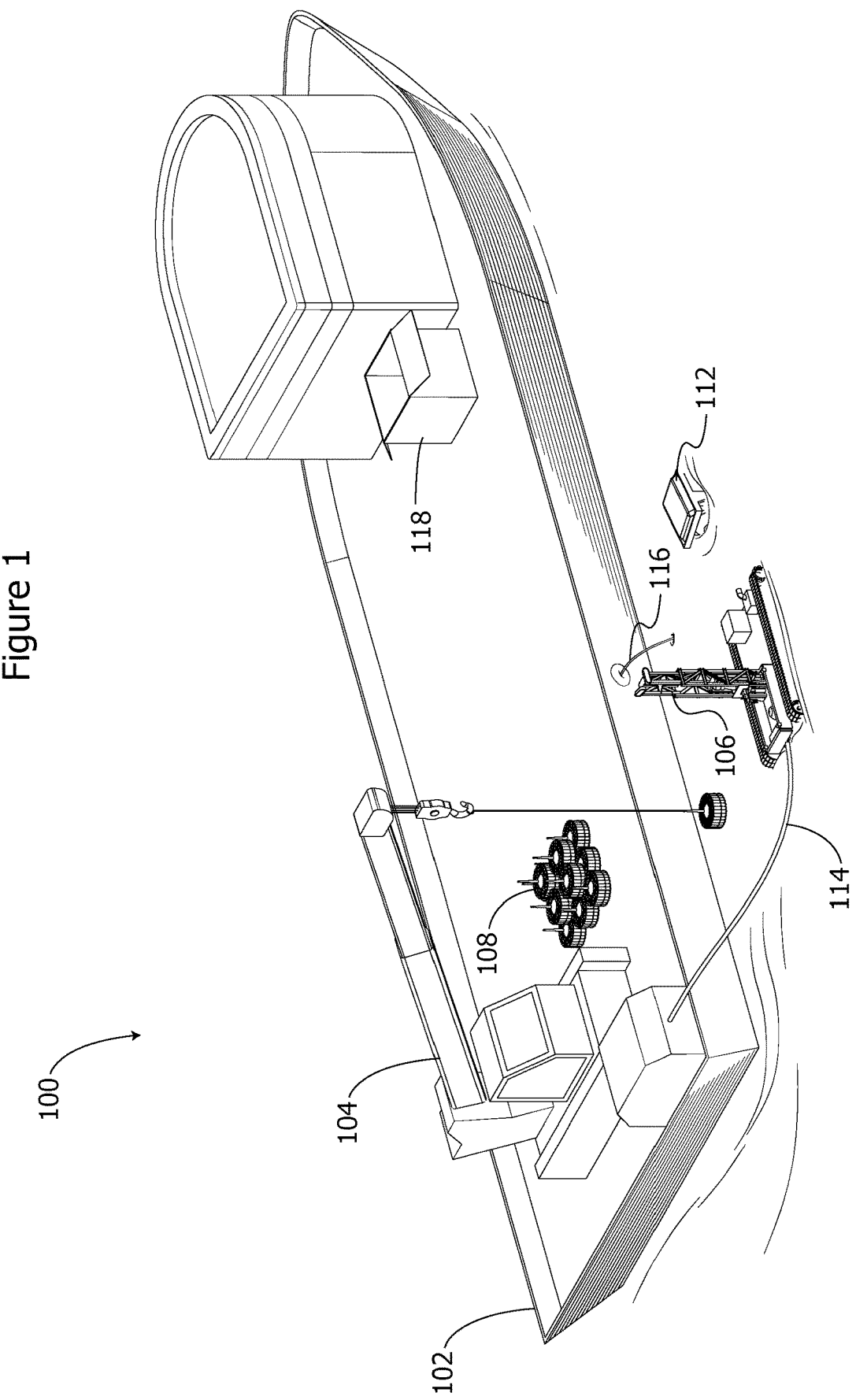
FIG. 1 is an environmental view of a geotechnical rig system deployed from a vessel, in accordance with an embodiment.

FIG. 1 is an environmental view of a geotechnical rig system deployed from a vessel, in accordance with an embodiment. A vessel system 100 includes, but is not limited to a vessel 102; a crane 104; a rig 106 including at least: a frame, and at least one docking base disposed on the frame; a plurality of interchangeable carousels 108 each with one or more addressed slots to stow one or more components and each being configured to exchangeably couple to the at least one docking base; and an arm 110 that is configured to controllably retrieve and/or position the one or more components.

In one embodiment, the vessel system 100 is used to implement a remotely operated rig 106, such as an unmanned amphibious geotechnical drilling and sampling rig for soil investigation and/or sampling, at locations where direct human interaction is undesirable or not possible due to logistical or environmental constraints.

In one embodiment, the vessel 102 is a barge, ship, boat, platform, floating rig, and/or other similar surface or subsurface vessel. The vessel 102 includes at least one crane 104, which is a mechanically, electrically, electromechanically, and/or engine/motor driven device for lifting, moving, lowering, or otherwise maneuvering one or more objects, including the one or more carousels 108, the rig 106, and/or an ROV 112. The rig 106 can be connected to the vessel via an umbilical cord 114 for power and/or communication.

In one embodiment, the vessel 102 transports the one or more carousels 108, the rig 106, and/or the ROV 112 to a desired location in an ocean, sea, lake, or other body of water, whereby the crane 104 deploys the rig 106 and/or the ROV 112 into the water. One of the carousels 108 can be deployed with the rig 106 or separately from the rig 106. The ROV 112 assists in the movement and/or positioning of the rig 106 from the vessel 102 to a seafloor, such as by using a guidewire 116 and/or heave compensation systems. The one or more carousels 108 can be transitioned from the vessel 102 to the rig 106 or from the rig 106 to the vessel 102 using the ROV 112, the guide wire 116, and/or and the crane 104. The one or more carousels 108 include one or more tools, sample vessels, and/or one or more drill casings; therefore, the rig 106 can use the resources of one carousel 108 on the seafloor for purposes of drilling and/or sampling and the one carousel 108 can be interchanged with one or more additional carousels 108 from the vessel 102 to extend the capabilities of the rig 106 on the seafloor while operating within load constraints of the crane 104, the ROV 112, the guide wire 116, heave compensation systems, and/or the umbilical cord 114, for example. While on the vessel 102, the carousels 108 are stackable on a deck, stowage compartment, and/or refrigeration unit, either before or after deployment on the rig 106. Any of the foregoing operations can be under complete or partial autonomous control using a computer system, circuitry, and/or programming. Alternatively, some or all of the operations can be manually effectuated or assisted.

In another embodiment, the vessel 102 comprises a vehicle, terrestrial vessel, or subterrestrial vessel, usable on or above land, underground or within tunnels, in an underwater environment, on or below a seafloor, and/or on another planet or cosmic body. The vessel 102 is illustrated as a water-based vessel for example purposes only, but the vessel 102 can be any device or system usable to deliver or deploy the rig 106 and/or one or more carousels 108 to a desired terrestrial and/or subterrestrial location. In other embodiments, the rig 106 can position itself in any terrestrial and/or subterrestrial environment independent of the vessel 102. In the embodiment where the vessel 102 comprises a ship, the vessel 102 can include a 120 ft work vessel with approximately 20 anchors and the crane 104, operating to approximately 2-3 k meters depth.

In a further embodiment, the rig 106 comprises a geotechnical drilling and/or sampling rig that remotely operates on or below a terrestrial or subterrestrial surface, such as a seafloor and/or subseafloor. The rig 106 can include propulsion systems to facilitate independent movement or positioning. Alternatively, the rig 106 can be moved or positioned entirely or partly by another system or device, such as the ROV 112. The rig 106 is configured to drill rock, clay, dirt, mud, or the like and/or obtain soil, solid, liquid, gas, and/or combination samples, using geotechnical drilling, sampling, and/or wireline techniques. For instance, a drill stick is driven into the surface using a combination of drill bits and casings with samples obtained using sample vessels. Wireline intervention can be utilized to interchange drill bits/tools and/or extend/retrieve sample vessels.

In certain embodiments, the rig 106 is at least partly enabled using the one or more carousels that are interchangeably coupled to the rig 106, which can be independently deployed to the rig 106 and/or retrieved from the rig 106 as needed or required. Thus, the rig 106 can launch independently of any of the carousels 108 or with one carousel 108 initially present. The rig 106 uses tooling, sample vessels, and/or casings from one of the carousels 108 to initiate, establish, or extend a drill stick and/or obtain a series of depth samples. The rig 106 can return sample vessels to the carousel 108, and the carousel 108 can be removed from the rig 106. The rig 106 can use additional carousels 108 to further extend, build, or deploy a drill stick and/or obtain additional samples, such as to an approximate depth of 75 to 100 meters or more. The extensibility of the rig 106 remotely is therefore provided while maintaining a smaller footprint and/or lower weight of the rig 106 itself.

In one embodiment, the ROV 112 transports the carousels 108 from the vessel 102 to the rig 106. The ROV 112 attaches to a lift point on the carousel 108 using assistance from the crane 104 and guides carousel 108 to the rig 106. The ROV 112 can be any robot or remote/automated controllable device, such as a LARS. However, it is contemplated that the one or more carousels 108 can be self-guided under independent propulsion to and/or from the rig 106 without requiring use of the ROV 112. Alternatively, the crane 104 or guide wire 112 can optionally be used to transport the one or more carousels 108 to and/or from the rig 106. In certain embodiments, the ROV 112 is a terrestrial vehicle or system that delivers and retrieves the one or more carousels 108 from a staging location and the rig 106. The staging location can include a vehicle, platform, container, climate-controlled unit, refrigeration unit, or the like. For instance, the rig 106 can be deployed to a mine or tunnel location and the ROV 112 can run exchanges of the carousels 108 from a staging container at or proximate to a mine entrance.

In certain embodiments, the one or more carousels 108 are staged or stored on a deck or surface area of the vessel 102. Optionally, one area of the deck or surface area of the vessel 102 is used for one or more carousels 108 ready for deployment to the rig 106 and a different area of the deck or surface area of the vessel 102 is used for one or more carousels 108 that have been returned from the rig 106. The ready-for-deployment carousels 108 include casings, vessels, and/or tools for extending a drill string of the rig 106. The returned or consumed carousels 108 include sample vessels associated with various depths, unused casings, and/or or returned tools. The carousels 108 are configured to be stackable with one another to conserve staging and/or storage space. For instance, the carousels 108 can include a flat bottom surface area that rests upon another of the carousels 108. Alternatively, a male/female mechanical coupling can be provided between adjacent carousels 108 to limit or prevent movement or shifting. Additionally, the portion of the carousels 108 can operate in conjunction with one another to define a space for containing a stacked carousel 108, such as in a pyramid type arrangement as illustrated. The carousels 108 may be confined using one or more frames to prevent or limit movement or shifting.

An optional refrigeration or climate-controlled container 118 is usable on the vessel 102, which container 118 is configured to receive and/or store one or more carousels 108 containing one or more sample vessels. The carousels 108 are stackable within the container 118 to preserve the sample vessel contents for testing and/or evaluation. The container 118 is programmed to maintain a specified temperature and/or humidity level or range. For instance, the container 118 is configured to maintain a sub-zero C temperature range to freeze any sample vessel contents. The container 118 includes an openable/closable roof or side portion to permit the lowering, sliding, driving, pushing, and removal of the carousels 108 using the crane 104 or other tug or vehicle device.

The vessel system 100 is exemplary and can be configured in a variety of ways. The crane 104 can be omitted or substituted with another lifting or hoist mechanism. The crane 104 can be movable and/or differently located on the vessel 102. Likewise, it is contemplated that a plurality of cranes 104 can be utilized for backup redundancy or to increase efficiency. Multiple rigs 106 and/or ROVs 112 can also be utilized to enable backup redundancy or to increase efficiency, such as by enabling simultaneous drilling and sample operations at one or more different sites.

Figure 2:
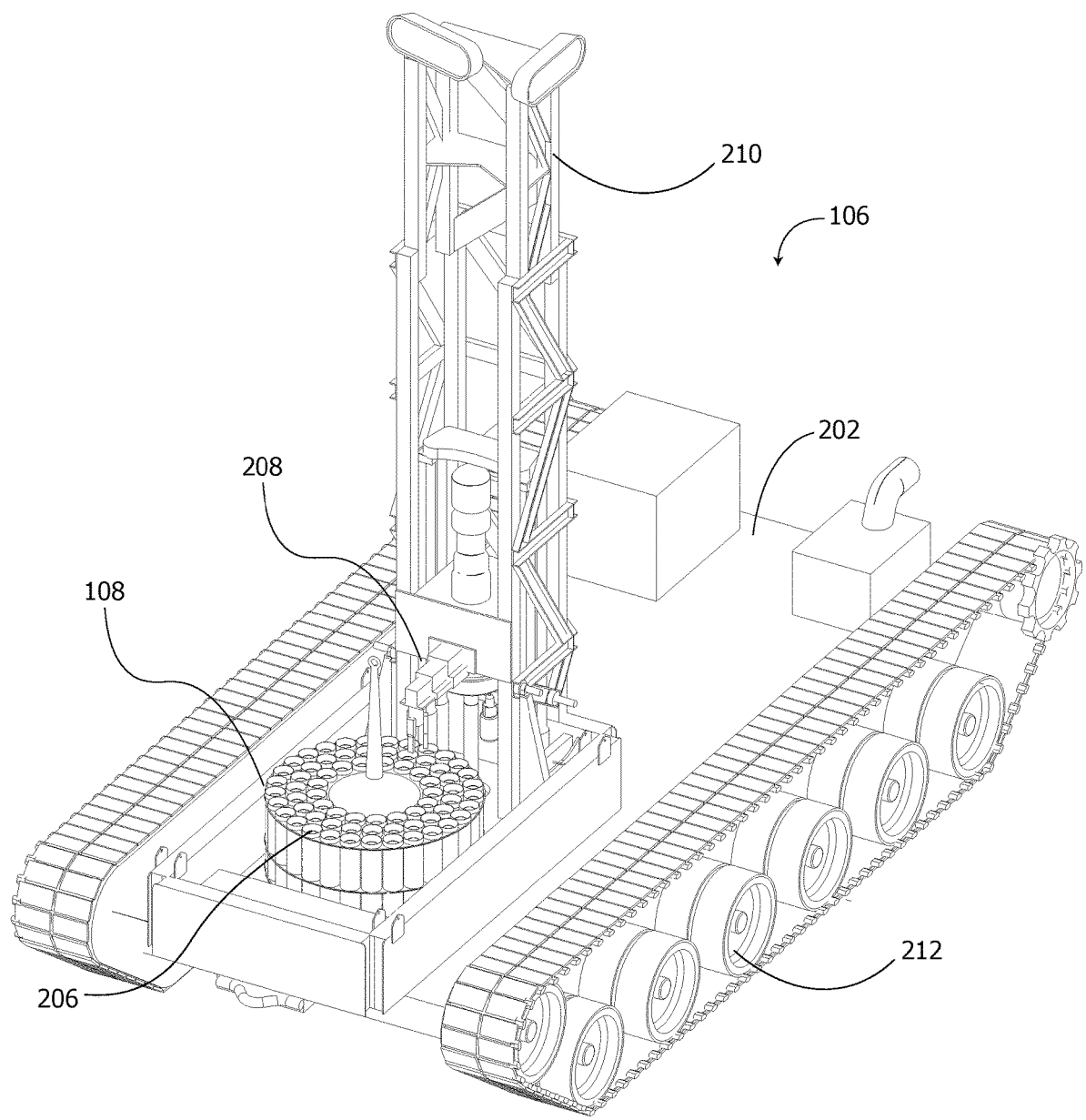
FIG. 2 is a perspective view of a geotechnical rig system, in accordance with an embodiment.

FIG. 2 is a perspective view of a geotechnical rig system, in accordance with an embodiment. In one embodiment, a rig 106 includes, but is not limited to, a frame 202 configured to deploy a drill string; at least one docking base 204 disposed on the frame 202; at least one carousel 108 with one or more addressed slots 206 to stow one or more components, the at least one carousel 108 being releasably coupled to the at least one docking base 204; and at least one arm 208 that is configured to controllably retrieve and/or position the one or more components.

In certain embodiments, the frame 202 is a structure composed of metal, fiberglass, carbon fiber, natural, synthetic, and/or composite material. The frame 202 provides support for the drill string and/or carousel 108 and includes at least one support member. The frame 202 can be configured as a sphere, cube, pyramid, square, circle, rectangle, or other similar geometric structure. Alternatively, the frame 202 can be a platform or a deck. In one particular embodiment, the frame 202 includes a mast 210 that extends substantially perpendicularly to support and/or protect the drill string and/or related components. The mast 210 forms a pyramidal, rectangular, cubical, cylindrical, or other similar structure that is at least partly open and/or exposed for accessing the drill string, for example. The mast 210 can be fixed or extensible and may be removable or omitted entirely from the frame 202. In certain embodiments, the frame 202 includes a plurality of masts 210. The frame 202 can be extensible or joinable with a plurality of additional frames 202 to provide an adjustable size, shape, and/or footprint. Additionally, the frame 202 can include one or more mounting points to attach and/or detach one or more components discussed herein, such as the mast 210, the docking base 204, the drill string, or the like, which can enable flexible customization of the rig 106.

In some embodiments, the rig 106 and frame 202 are configured to rest directly on a seafloor, ground surface, other terrestrial or subterrestrial area, or cosmic body. One or more stands or support members are also contemplated, which one or more support members can be length or angularly adjusted for accommodating irregular surface features and/or leveling the rig 106. The one or more stands or support members can be located in or proximate to one or more corners of the frame 202. Additionally, the one or more stands or support members can be disposed along one or more edges of the frame 202 or positioned underneath the frame 202. In one particular embodiment, the rig 106 includes a propulsion system 212, such as an electric, gasoline, diesel, hybrid, or other similar engine or motor driven system. The propulsion system 212 is configured to enable the rig to be remotely and/or autonomously positioned, repositioned, deployed, recaptured, moved, or the like. One specific type of the propulsion system 212 includes a continuous track propulsion system, but one or more metal or rubber wheels or tires are also contemplated. Additionally, the rig 106 may include a passive mobilization system, such as rollers, wheels, or tracks that are not engine or motor actuated. Instead, the rig 106 can be pulled, pushed, or otherwise manipulated using a tow or tug device, such as an ROV, vehicle, ship, stationary rig, and/or other system or device. The passive mobilization system can be engaged and/or disengaged using mechanical, electromechanical, or electrical systems to switch between mobile and immobile fixed modes.

In one embodiment, the rig 106 includes an umbilical cord 114 for remote power, communication, control, data, and/or physical tethering. For instance, the rig 106 can be connected to the vessel 102 via umbilical cord 114. The umbilical cord 114 in this context is retractably deployed as the rig 106 is lowered to the seafloor, for example. However, it is conceived that the umbilical cord 114 can be functionally altered and/or omitted. For example, the umbilical cord 114 may provide tethering functions whilst communication is handled wirelessly. Alternatively, power may be provided to the rig 106 via an onboard or nearby battery whilst the communication and tethering is handled via the umbilical cord 114. The rig 106 may be independent of any umbilical cord 114.

Figure 3:
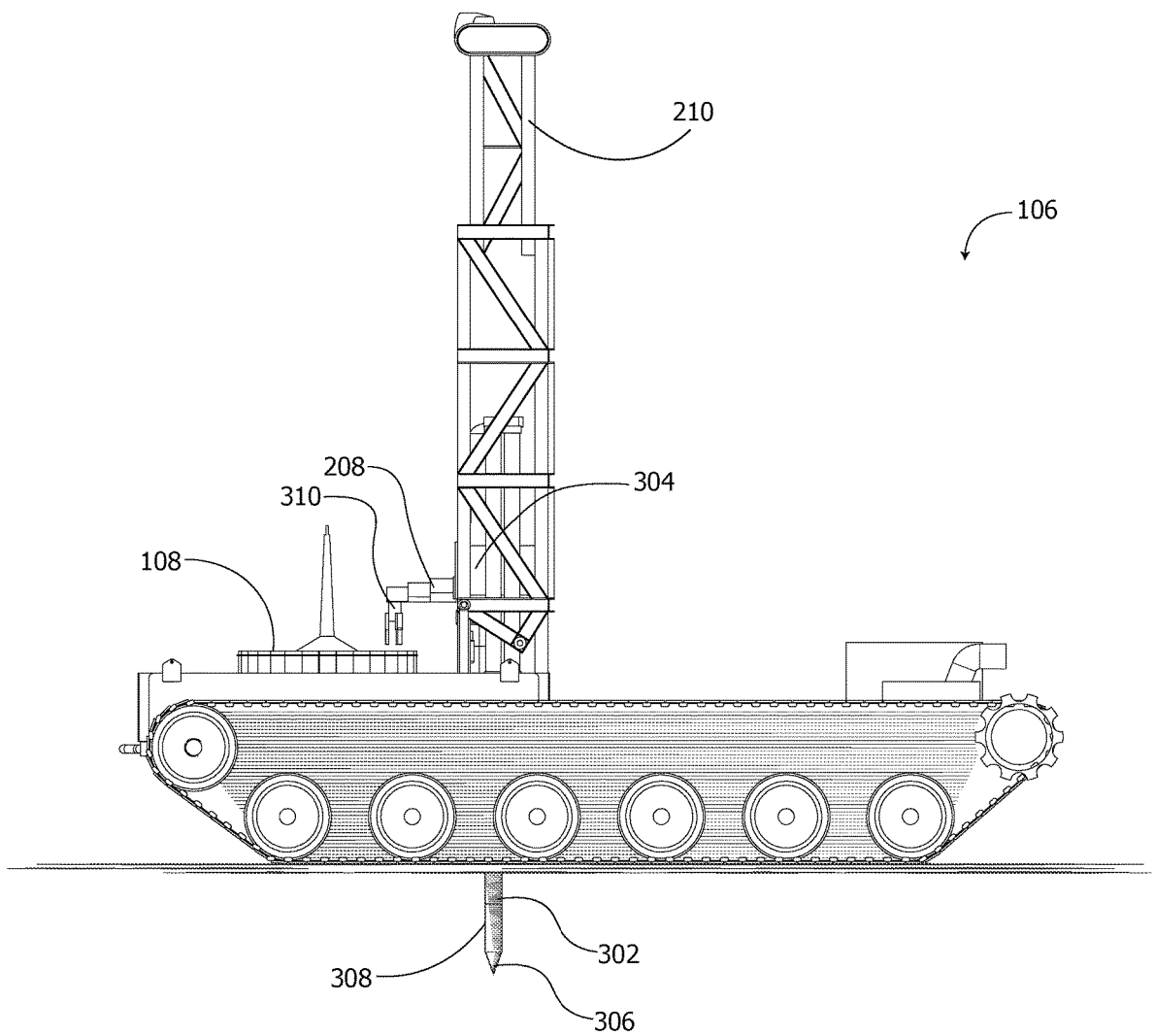
FIG. 3 is a side view of a geotechnical rig system, in accordance with an embodiment.

FIG. 3 is a side view of a geotechnical rig system, in accordance with an embodiment. In one embodiment, a rig 106 includes, but is not limited to, a frame 202 configured to deploy a drill string; at least one docking base 204 disposed on the frame 202; at least one carousel 108 with one or more addressed slots 206 to stow one or more components, the at least one carousel 108 being releasably coupled to the at least one docking base 204; and at least one arm 208 that is configured to controllably retrieve and/or position the one or more components.

In one embodiment, the rig 106 is configured to deploy a drill string 302, which is composed of one or more segment casings 308 and/or a drill head 306. The rig 106 includes a rotational drive system 304 to forcibly thrust, rotate, and/or retract the drill string 302 and/or drill head 306 to enable drilling and/or sampling in a seafloor, subseafloor, terrestrial surface, terrestrial subsurface, or other cosmic body, thereby allowing for sample collection in nearly any hard or soft ground formation, such as ultra-soft silts, soil, rock, clay, mud, or the like. Sampling can be accomplished via the drill string 302 using traditional wireline intervention methods using any of the following devices: push sample, piston sample, core barrel, tube sample, vented tube, Shelby tube, and/or non-coring assembly cap. In addition to physical sampling the rig 106 can deploy a range of data collection tools such as CPT, 5-15 $cm^2$ Cones, Ball Cone, T-bar, Pizo Probe, Gama, seismic, and the like. As such, the rig 106 provides up to a full spectrum of down hole tooling, drilling, and/or sampling with wireline intervention and/or stick drilling methods.

In certain embodiments, the drill string 302 is approximately 2 meters to 150 meters in length, but may be longer, shorter, and/or extensible. The drill string 302 is composed of a plurality of the segment casings 308 with each segment casing screwing via threads into an adjoining casing to enable an increase or decrease of an overall length of the drill string 302. In many embodiments, approximately 30 casings to 60 casings are included in a single drill string 302. Each segment casing 308 is approximately 1 m to 3 m in length, such as 2 m, but other lengths are possible. The casings 308 are typically formed from metal, such as metal piping, and the drill string 302 is hollow due to the segment casings 308 being hollow, but solid and/or semi-solid portions of the drill string 302 are within the scope of the disclosure. The diameter of the drill string is typically approximately between 2 inches and 8 inches, such as between 2 inches and 4 inches, but other diameters are within the scope of the present disclosure.

In one embodiment, the drill head 306 is disposed on a leading portion of the drill string 302 and is configured to support and/or incorporate a drill bit and/or non-coring assembly cap. The drill bit can include diamond and/or sawtooth type bits, or other bits, and can be interchanged, installed, or removed via known techniques such as wireline intervention. The drill bit can be approximately 2 inches to 8 inches in length, such as 5 to 6 inches in length, but other sizes are within the scope of the present disclosure.

In one embodiment, the arm 208 is configured to facilitate operations involving the carousel 108 and the drill string 302. The arm 208 can be movable, extensible, rotatable, retractable, or otherwise fixed or movable. In certain embodiments, the arm 208 includes a shuttle head 310 that travels along or with the arm 208, such as along or with a series of extensions, a beam, channel, or other member. The shuttle 310 head can be movable, extensible, retractable, rotatable and/or can include a friction, fingers, claps, or pressure grip mechanism to releasably pickup one or more components. In certain embodiments, the carousel 108 is configured with one or more indexed slots to store and receive any of tooling, sample vessels, or segment casings 308. The carousel 108 rotates to expose any of the one or more indexed slots to the arm 208 and/or shuttle head 310. The carousel 108, the arm 208, and/or shuttle head 310 operate under automated and/or remotely controlled instructions without requiring manual direct in-person intervention, to perform operations including installation and removal of segment casings 308 from the drill string 302, deployment and withdrawal of sample vessels, and/or installation or removal of tooling. For instance, the shuttle head 310 can extend to a programmed or user-defined position and drop or catch a component from the carousel 108. The shuttle head 310 can then return to a position over the drill string 302. The shuttle head 310 can drop or install the component into or on the drill string 302. Other operations and techniques are further described herein.

Figure 4:
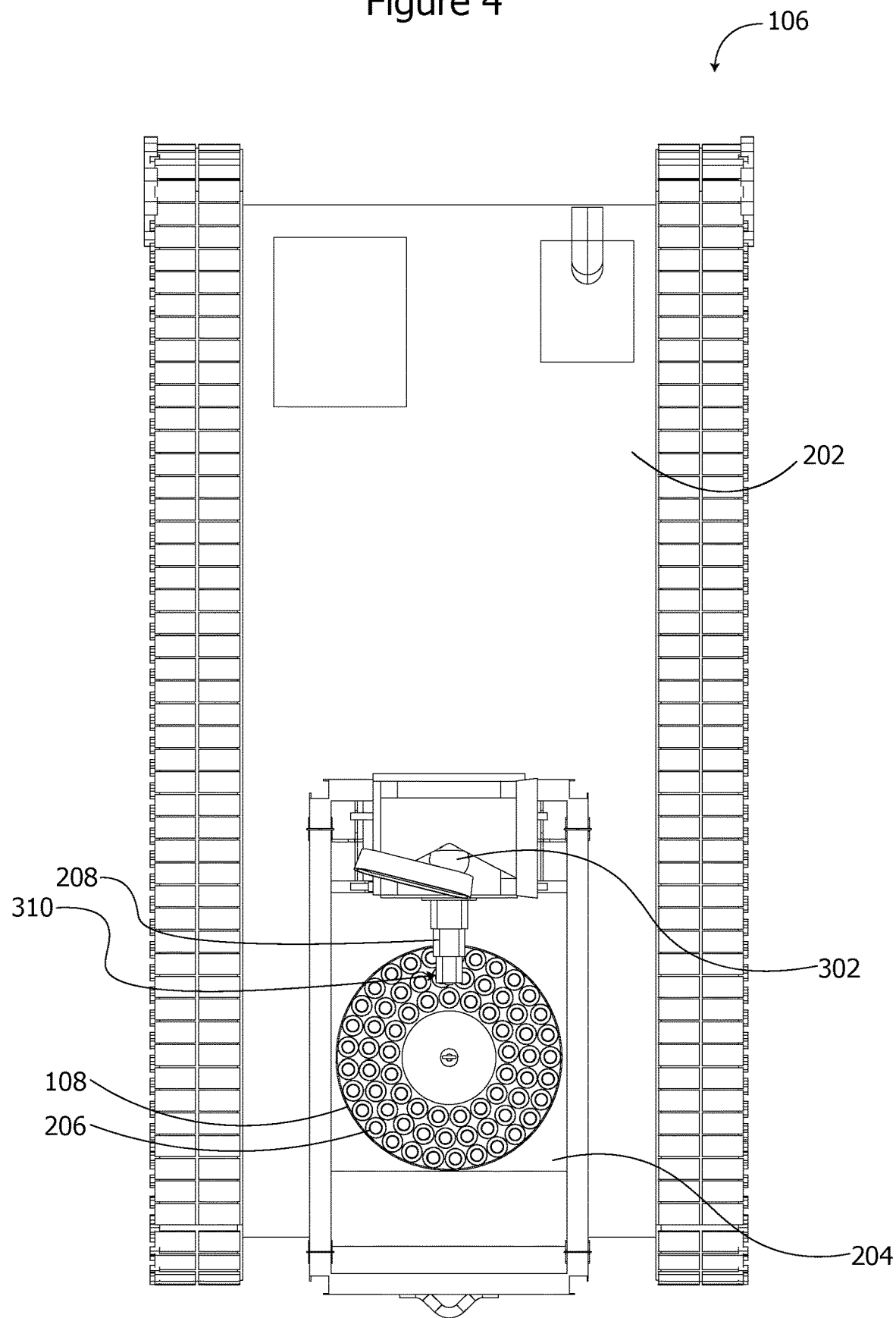
FIG. 4 is a top view of a geotechnical rig system, in accordance with an embodiment.

FIG. 4 is a top view of a geotechnical rig system, in accordance with an embodiment. In one embodiment, a rig 106 includes, but is not limited to, a frame 202 configured to deploy a drill string 302; at least one docking base 204 disposed on the frame 202; at least one carousel 108 with one or more addressed slots 206 to stow one or more components, the at least one carousel 108 being releasably coupled to the at least one docking base 204; and at least one arm 208 that is configured to controllably retrieve and/or position the one or more components.

In one embodiment, the carousel 108 includes a plurality of addressed or indexed slots 206. The slots 206 are cavities, tubes, boxes, depressions, boundaries, containers, and/or other spaces for presenting and/or storing one or more components at one or more known positions. Each of the slots 206 are addressed, indexed, plotted, marked, or otherwise identifiable. For instance, the slots 206 may each be identified by a Cartesian coordinate to its center relative to a starting or relative point. Alternatively, each slot may be identified by a number of stepper or other motor increments from a starting or relative point. Because the carousel 108 rotates in certain embodiments relative to the docking base 204, another option is for each slot to be identified by a rotational degree or increment plus a radius distance from center or equivalent. Whichever addressing or identification scheme is selected, the slots 206 are in some embodiments identifiable to enable access to and/or depositing of components therein. Thus, the addressing or identification of the slots 206 include two and/or three dimensions with rotation as an optional fourth dimension.

In other embodiments, each of the carousels 108 can be identical, individualized, or identifiable by group or category, with different arrangement, positioning, sizes, or orientations of the slots 206. In the case of individualized or group/category type carousels 108, a marking, RFID-type tag, beacon, or other indicia can be used to identify the type and/or determine the appropriate addressing or identification system for the particular carousel 108. A camera, beacon scanner, barcode reader, or other sensor is configured to read the indicia and a processor uses the data retrieved to match up with the carousel type to determine the matching schema for addressing or identification.

In one particular embodiment, the carousel 108 can be indexed or keyed to the docking base 204 to establish the slots 206 in the addressing or identification system. In one particular embodiment, the carousel 108 includes a calibration point to establish, confirm, or adjust the starting position or relative position for the addressing or identification system.

In further embodiments, the carousel 108 is configured to rotate about a center axis to turn relative to the docking base 204 and/or the frame 202 of the rig 106. The arm 208 includes the shuttle head 310 that traverses between the drill string 302 along a path toward a center of the carousel 108. The carousel 108 rotates relative to the arm 208 and/or the shuttle head 310 enabling access by the shuttle head 310 to the slots 206. Alternatively, the arm 208 can include a robotic arm that moves in two and/or three dimensions with a pickup head that can reach one or more of the slots 206. In this embodiment, the carousel 108 may be fixed, rotatable, or partially movable as the robotic arm can provide additional range of movement and access. The arm 208 is depicted as mounted and extends from the frame 202, but it is also contemplated that the arm 208 can be mounted to the carousel 108 and extend toward the drill string 302. In this particular embodiment, the arm 208 can rotate from a center or edge position of the carousel 108 and traverse radially to the one or more slots 206.

In various embodiments, the components presented, maintained, or stowed in the slots 206 can include any one or more of drill casings segments, sample vessels, drill bits, and/or tools that are usable for drilling, sampling, or otherwise investigating formations or material. Each of the slots 206 can include a single component or a plurality of components. Also, each of the slots 206 can be dedicated to particular component or the contents of the slots 206 can change during the course of operation of the rig 106 during a particular mission, such as when stick drilling advances and samples are obtained. The arrangement of the slots 206 can include a radial pattern of concentric circles, a grid, one or more rows, or another regular or irregular pattern. Additionally, the slots 206 can be differently positioned and/or accessible, such as vertically, horizontally, obliquely from a top, bottom, inside, and/or side of the carousel 108.

In operation, for example, the carousel 108 has slots 206 that are loaded with casings, sample tubes, drill heads, drill bits, caps, vessels, tools, and/or components. The carousel 108 is then lowered onto the docking base 204. The shuttle head 310 moves to computer addresses associated with the slots 206 with the carousel 108 rotating to facilitate access to the slots 206. The shuttle head 310 picks up one or more components and retrieves such for installation or deployment to or within the drill string 302. Likewise, the shuttle head 310 returns one or more components, such as material samples at different known depths, back to the carousel 108 into one or more addressed slots 206. The carousel 108 rotates therewith to receive the returned components into particular slots 206. The consumed carousel 108 with any returned components, such as sample tubes, is then removed from the docking base 204 and returned for restocking and/or further processing. Computer memory or data transmissions are maintained or made to record provenance data for the one or more slots 206, including, for example, content identification, date and time stamp, depth of any associated sample vessel or tube, temperature or climate information, pressure relief or venting actions taken, or other useful information for future investigation and/or analysis.

Figure 5:
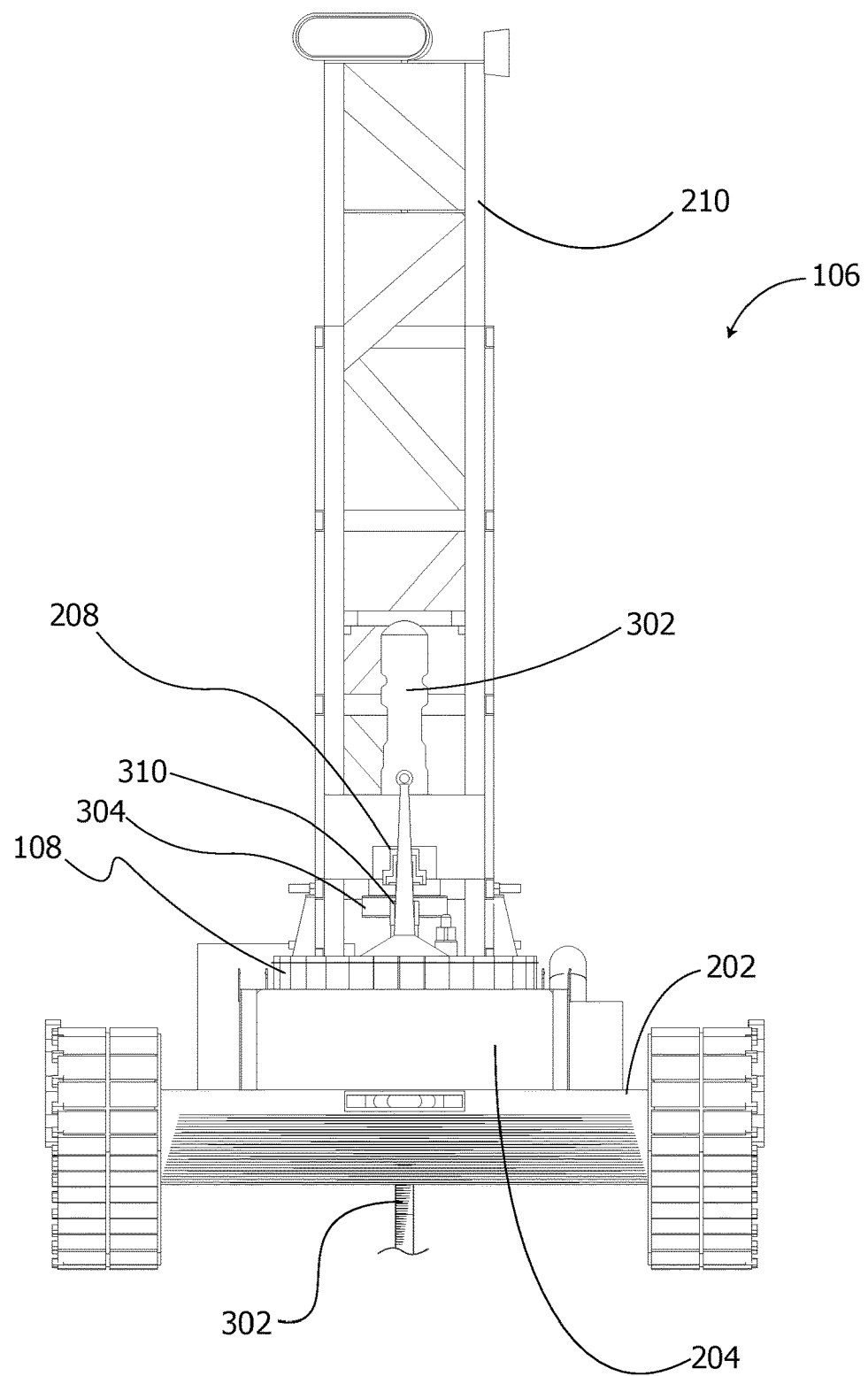
FIG. 5 is a front view of a geotechnical rig system, in accordance with an embodiment.

FIG. 5 is a front view of a geotechnical rig system, in accordance with an embodiment. In one embodiment, a rig 106 includes, but is not limited to, a frame 202 configured to deploy a drill string 302; at least one docking base 204 disposed on the frame 202; at least one carousel 108 with one or more addressed slots to stow one or more components, the at least one carousel 108 being releasably coupled to the at least one docking base 204; and at least one arm 208 that is configured to controllably retrieve and/or position the one or more components.

In certain embodiments, the at least one arm 208 is configured to attach and/or remove one or more drill casings on the drill string 302. The drill string 302 includes a drill head and a drill stick that is composed at least in part from the one or more drill casings. The drill string 302 can extend anywhere from approximately 1 meter to approximately 150 meters or more into a terrestrial, subterrestrial, or cosmic body or subsurface from the rig 106. The rotational drive 304 is configured to apply torque to the drill string 302 to facilitate thrusting and/or retraction of the drill string 302 into the surface or subsurface. In one particular embodiment, the drill string 302 is fully or partly buildable and/or extensible by the rig 106; likewise, the drill string 302 is fully or partly deconstructable and/or reducible by the rig 106. This modularity is accomplished at least in part by the casings being removably coupled or joined to adjoining drill casings, with the lead casing being coupled or joined to the drill head. Mating threads are used to screwably join the drill casings and the drill head although a different fastening mechanism is within scope of the present disclosure. A supply of casings is provided by the carousel 108 using the arm 208 and/or the shuttle head 310 to install the casings on the drill string 302. Likewise, when deconstructed, the casings are removable from the drill string 302 and deposited to the carousel 108. Because the carousel is removable, refillable, exchangeable, and/or interchangeable, an overall length of the drill string 302 is not substantially limited except by other constraints, such as motor or drive torque. In operation, the shuttle head 310 extends to the carousel 108 to retrieve a casing and returns the casing to an end of the drill string 302. The shuttle head 310 can rotate and/or the rotational drive 304 can rotate to facilitate installation of the casing onto the drill string. A reverse sequence of operations is implemented to break down and/or deconstruct the drill string 302. For instance, the shuttle head 310 can secure to an end of the drill string and rotate, or the rotational drive 304 can rotate, to back off a casing from an end of the drill string 302. The shuttle head 310 can return the casing to the carousel 108.

In a further embodiment, the at least one arm 208 is further configured to extend or retrieve one or more sample vessels via the drill string 302. The drill string 302 is at least partly hollow when constructed to enable deployment of sample vessels to the drill head and retrieved therefrom for sample collection at particular depths. The sample vessels can include tubes or other containers and can be lowered and/or retrieved using typical wireline intervention techniques, with check valves or vents provided as needed. In addition to physical sampling, the rig 106 can deploy a range of data collection tools such as CPT, 5-15 $cm^2$ Cones, Ball Cone, T-bar, Pizo Probe, Gama, seismic, and the like to provide up to a full spectrum of down hole tooling, drilling, and/or sampling. A particular sample vessel can be served empty by the carousel 108 with the shuttle head 310 extending via the arm 208 to pick-up the sample vessel from one or more slots. The sample vessel can then be deployed whereby the shuttle head 310 positions the sample vessel for release through the drill string 302. A filled sample vessel can be similarly returned from the drill string 302 to the carousel 108 using the shuttle head 310. The sample vessels can be stored in a configured and/or programmed arrangement to facilitate identification of an order and/or a depth associated with a sample contained within the sample vessel. Because the carousel is exchangeable, interchangeable, and/or retrievable before, during, or after operation of the rig 106, the sample vessels can be collected to enable more detailed investigation and/or analysis. A stocked carousel 108 with filled vessels can be removed from the docking base 204 and replaced with a new carousel 108 having empty sample vessels to continue the sample process as the drill string 302 progresses.

In certain embodiments, the sample vessels and the casings are configured to share a single slot in the carousel 108 to conserve space. For instance, the sample vessel is positioned inside the casing within one slot to enable the casing or the sample vessel to be removed and/or returned independently. In operation, the casing is retrieved by the shuttle head 310 and installed on the drill string 302. Subsequently, the sample vessel from the same slot is retrieved by the shuttle head 310 and deployed via the drill string 302 for sample collection. The sample vessel with content from a particular drill depth can be returned to the carousel 108 and positioned in the same slot. This ordered sequence of operations is repeated as required.

In other embodiments, one or more tools can occupy one or more slots of the carousel 108 or can be positioned elsewhere on the rig 106. The shuttle head 310 extends via the arm 208 to capture a particular tool and introduce the tool to the drill string, whereby it can be lowered for use, installation, or operation as required, such as using wireline intervention techniques. The shuttle head 310 can return the tool to the carousel 108 or other position on the rig 106. The replaceability and/or exchangeability of the carousel 108 enables introduction of tooling to the rig 106 while the rig 106 is remotely situated and/or in operation.

No direct human or in-person presence is required on the rig 106 to exchange a carousel 108, extend or reduce the drill string 302, deploy or retrieve sample vessels, and/or implement or install tooling. The rig 106, shuttle head 310, arm 208, carousel 108, rotational drive 304, and other referenced components can operate automatically or under remote control or using program instructions, computer circuitry, storage memory, and/or a network or a wireless interface. Operation of the rig 106, shuttle head 310, arm 208, carousel 108, rotational drive 304, and other referenced components can be recorded, stored, and/or transmitted for remote real-time or delayed analysis using the computer circuitry, storage memory, and/or network or a wireless interface.

Figure 6:
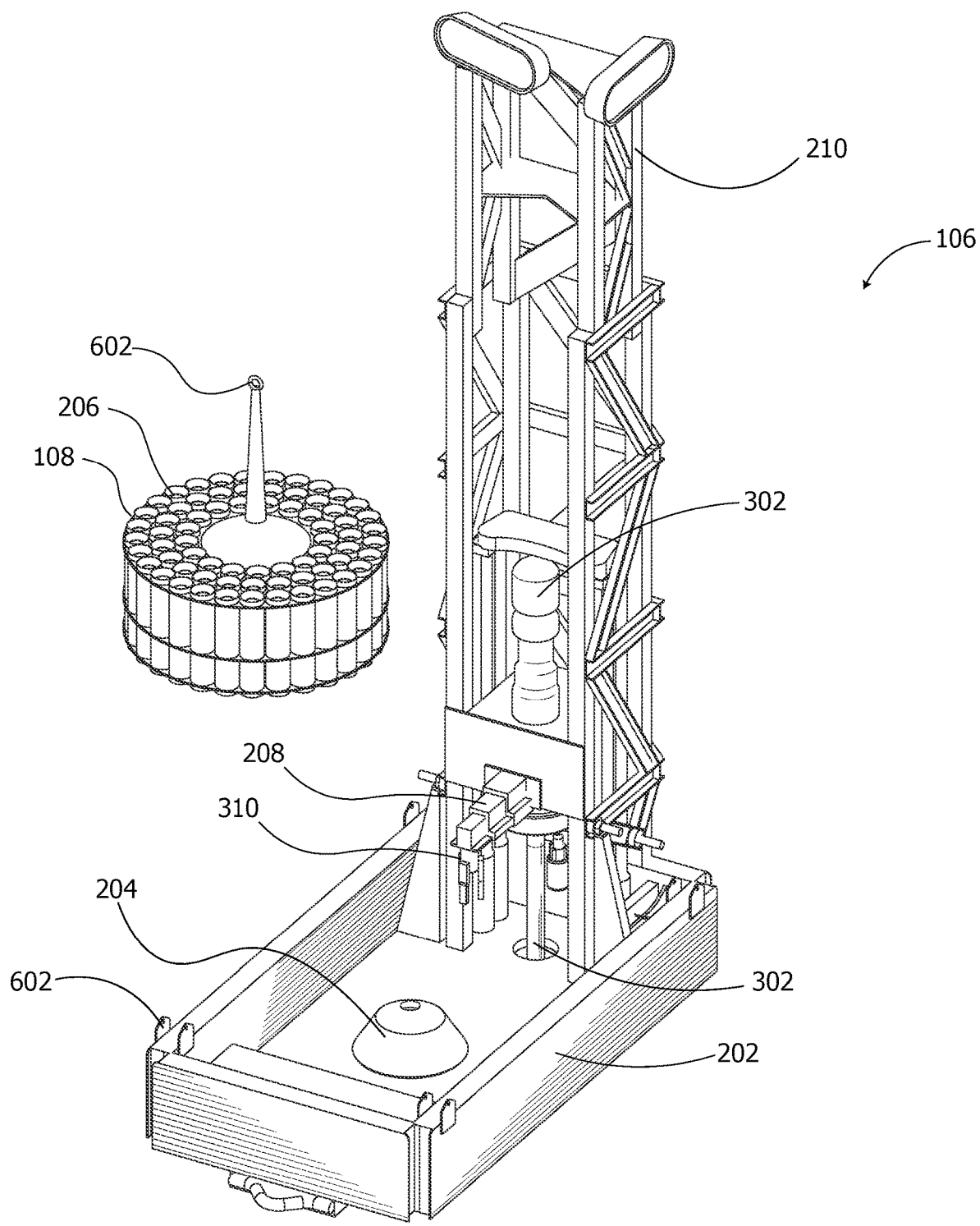
FIG. 6 is an exploded view of a geotechnical rig system, in accordance with an embodiment.

FIG. 6 is an exploded view of a geotechnical rig system, in accordance with an embodiment. In one embodiment, a rig 106 includes, but is not limited to, a frame 202 configured to deploy a drill string 302; at least one docking base 204 disposed on the frame 202; at least one carousel 108 with one or more addressed slots 206 to stow one or more components, the at least one carousel 108 being releasably coupled to the at least one docking base 204; and at least one arm 208 that is configured to controllably retrieve and/or position the one or more components.

In one embodiment, the frame 202 is configured to be stationary without a propulsion system. The frame 202 includes one or more frame lift points 604 that are usable to lower, lift, set, reposition, and/or move the rig 106 using a crane, hoist, ROV, or other external load supporting system, device, vessel, or vehicle. The frame 202 can be deposited on another platform, vehicle, or vessel to enable mobility. Alternatively, the frame 202 can be positioned directly on a terrestrial, subterrestrial, or cosmic body impendent of any vehicle or vessel. In certain embodiments, the frame 202 includes legs or supports, which can be pivotable, angled, or adjustable to accommodate irregular features and/or assist in leveling the rig 106. The frame 202 is usable in conjunction with one or more anchors to prevent and/or limit movement or shifting of the rig 106.

In one particular embodiment, the frame 202 includes the docking base 204 which is configured in a conical and/or funnel shape to removably receive the carousel 108. The carousel 108 is removable and/or positionable on the docking base 204 using an alignment mechanism to initialize the carousel to a correct rotational orientation relative to the docking base 204. The alignment mechanism can include a key, male/female interconnection, ball sockets, a magnetic system, and/or calibration markings or indicia. The carousel 108 snaps, locks, or latches automatically when lowered onto the docking base 204, such as when in the correct alignment. The carousel 108 can be removed from the docking base 204 using wireline intervention or another electromechanical or mechanical release system. Other forms of the docking base 204 are contemplated and within the scope of the present disclosure. These include a rotational platform, threaded platform, a post and/or socket, a suspension arm or coupling, one or more wheels or bearings, or another mechanism that facilitates removable positioning of the carousel 108 onto the frame 202.

In some embodiments, the carousel lift point 602 is configured as a hook, eyelet, ring, slot, or other point to attach a load support device, system, line, or object for lifting, lowering, maneuvering, twisting, or otherwise manipulating the carousel 108 independent of the rig 106. The lift point 602 can be positioned on a bale or other extension projecting from a medial or center area of the carousel 108. Alternatively or additionally, the carousel 108 can include one or more perimeter, edge, side, or bottom mounting points. The lift points 602 can include a cable, line, rope, or other flexible extension. Maneuvering points, lines, and cables are also within the scope of the present disclosure. The rig 106 can be lowered and installed with less weight and/or load, with or without an initial carousel 108 present. Subsequently, during operation of the rig 106, a sequence of carousels 108 are separately or independently lowered for staging or immediate installation on the docking base 204. The components of the carousel 108 are consumed and/or used by the rig 106 as needed. Thereafter, consumed or refilled carousels 108 can be separately retrieved and removed from the docking base 204 and replaced with new and/or replenished carousels 108.

In further embodiments, the docking base 204 is configured to rotate in a clockwise and/or counterclockwise manner using an electric, hydraulic, gasoline, diesel, electromagnetic, or other type of system, motor, or engine. The docking base 204 can optionally shift, project, rescind, or otherwise move in one or more various other dimensions. A computer processor, circuitry, computer program instructions, storage memory, communication or network interface, and/or other electronic components are used to implement, select, and/or execute specific movements and/or rotations of the docking base 204 to effectuate positioning of the carousel 108. Optionally, the carousel 108 can be configured to rotate in a clockwise and/or counterclockwise manner using an electric, hydraulic, gasoline, diesel, electromagnetic, or other type of system, motor, or engine that is incorporated within the carousel 108. In this embodiment, a computer processor, circuitry, computer program instructions, storage memory, communication or network interface, and/or other electronic components are used to implement, select, and/or execute specific movements and/or rotations of the carousel 108 relative to the docking base 204 to effectuate positioning of the carousel 108.

Figure 7:
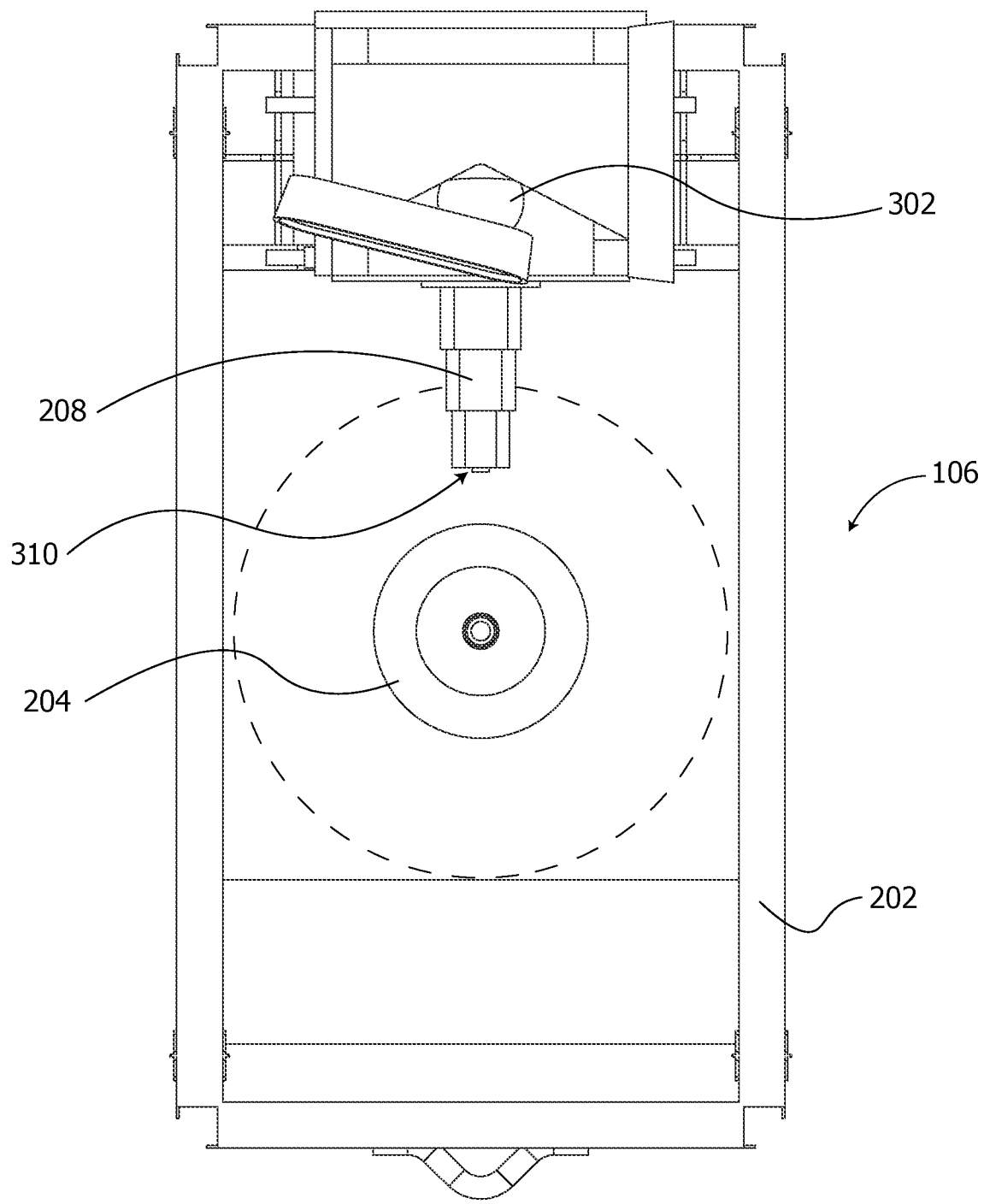
FIG. 7 is a top view of a geotechnical rig with an interchangeable carousel system, in accordance with an embodiment.
Figure 8:
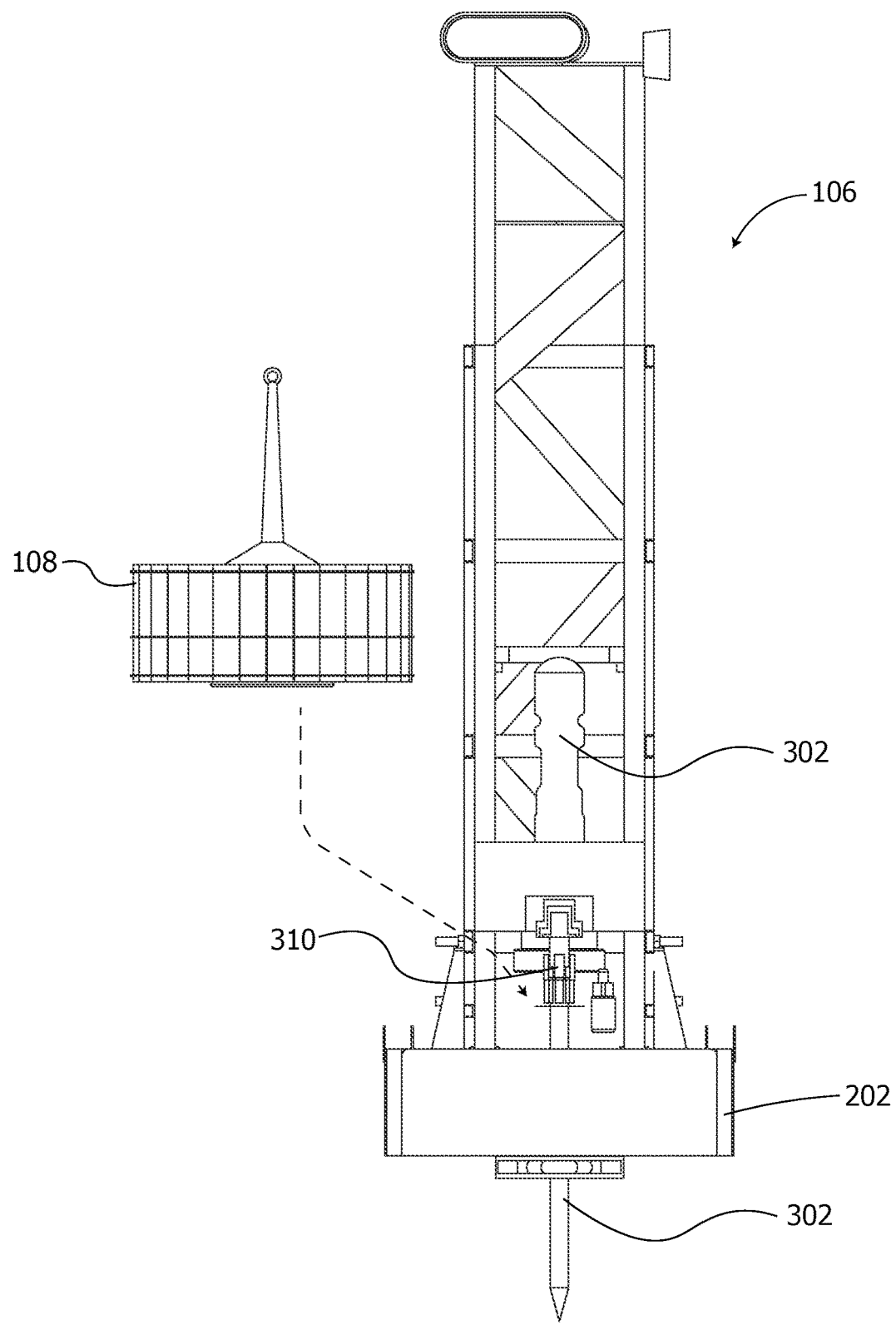
FIG. 8 is a front view of a geotechnical rig with an interchangeable carousel system, in accordance with an embodiment.
Figure 9:
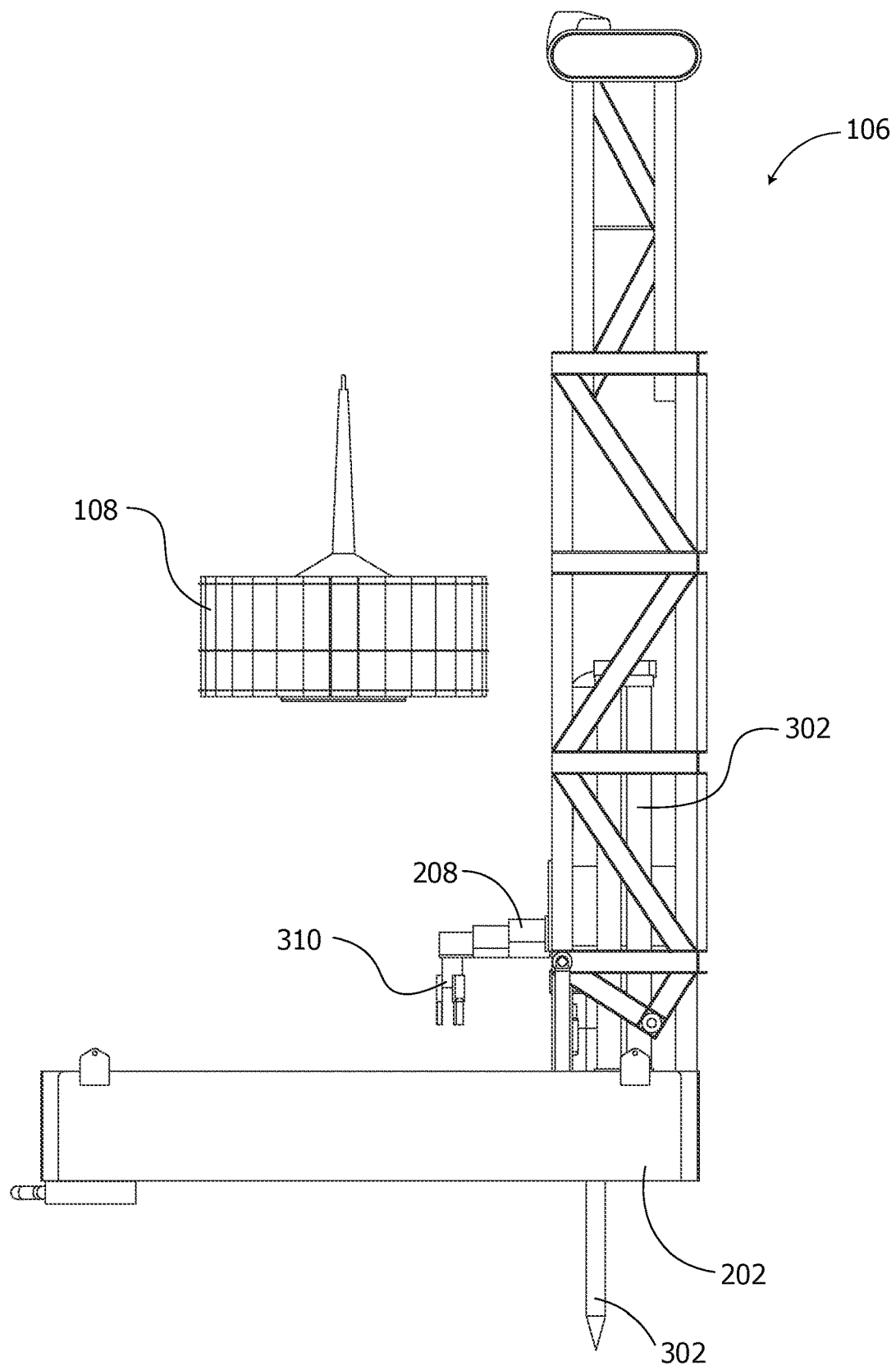
FIG. 9 is a side view of a geotechnical rig with an interchangeable carousel system, in accordance with an embodiment.

FIGS. 7-9 are top, front, and side views respectively of a geotechnical rig with an interchangeable carousel system, in accordance with an embodiment. In one embodiment, a rig 106 includes, but is not limited to, a frame 202 configured to deploy a drill string 302; at least one docking base 204 disposed on the frame 202; at least one carousel 108 with one or more addressed slots 206 to stow one or more components, the at least one carousel 108 being releasably coupled to the at least one docking base 204; and at least one arm 208 that is configured to controllably retrieve and/or position the one or more components.

In certain embodiments, a process or system for carousel exchange is provided. To begin, the rig 106 is positioned at a remote terrestrial or subterrestrial site without a carousel 108; although an initial carousel may be installed with the rig 106. One or more operators is not required to physically man the rig 106 and can remain offsite from the rig 106, such as on a remote vehicle, vessel, or at another location. One or more carousels 108 are similarly maintained offsite from the rig 106 and transitioned to the site of the rig 106 for loading via the docking base 204 using an unmanned vehicle such as an ROV. The carousels 108 provide tooling, sample vessels, casings, drill bits, or other components that are usable by the rig 106. The arm 208 and/or shuttle head 310 operate between a carousel 108 and the drill string 302 to extend and/or collapse the drill string 302; remove, deploy, and/or exchange tooling from the drill string 302; deploy and/or retrieve sample vessels from the drill string 302; install and/or activate sensors or devices with the drill string 302; or perform other operation as described herein. Subsequently, a consumed or used carousel 108 is removed from the rig 106 and optionally replaced by another carousel 108 to restock the rig 106. The rig 106 can continue at the remote site to perform sampling, investigation, drilling, and/or other geotechnical operations while continually being replenished and/or restocked with one or a series of carousels 108. A consumed or used carousel 108 that is removed from the rig 106 can be transitioned offsite from the rig 106, such as back to a remote vehicle, vessel, or other locale, whereby the carousel 108 can be stored, such as in a climate controlled container, used for scientific or research purposes, restocked, repaired, and/or used for other technical operations.

In some embodiments, the drill string 302 is partially established with one or more initial casings 308 and a drill head 306 that extend via the rotational drive 304. The shuttle head 310 is then able to extend the drill string 302 using one or more casings 308 picked up from the carousel 108, such as by screwing a new casing 308 onto an established casing 308 with the rotational drive 304 advancing the drill string 302.

In further embodiments, the carousel 108 is lowered, raised, transitioned, and/or retrieved using support from an external vehicle or vessel, such as a crane, guide wire, or unmanned vehicle. Alternatively, the carousel 108 can include a propulsion system such as wheels, continuous track wheels, jets, releasable ballasts or weights, or another motorized system. The carousel 108 can guide itself to and/or from the rig 106 using computer programmed autonomous instructions or remote control operations.

In additional embodiments, the rig 106 includes a plurality of docking bases 204 and is configured to include a plurality of carousels 108 mounted on the rig 106 at any given time. The docking bases 204 can operate on a turntable to rotate different carousels 108 into active position with each carousel being rotatable relative to a traversing shuttle head 310.

In yet a further embodiment, the carousel 108 can be differently mounted relative to the rig 106. For instance, the carousel 108 can be positioned on its side and rolled to expose different slots to the shuttle head 310. Alternatively, the carousel 108 can be fixed and the arm 208 can be a robotic arm with additional range of movements to pick up components from virtually any fixed location on the carousel 108. The carousel 108 can optionally include one or more inner compartments or a stacked set of carousels 108 with the inner compartments that are exposable to provide access to additional slots and/or components.

In another embodiment, a sleeve composed of a plurality of stacked or otherwise joined carousels 108 can be utilized during migration or transitioning to and/or from a site of the rig 106. The sleeve is placed proximate to the rig 106 to stage the carousels 108. Individual carousels 108 can be moved from the sleeve to the rig 106 for use. Subsequently, a set of consumed carousels 108 can be returned or retrieved from the site of the rig 106 as a sleeve.

In yet another embodiment, the carousel 108 is not required to dock on the rig 106 and instead floats, rests, hangs, or is otherwise disposed nearby the rig 106. The arm 208 can retrieve and/or return one or more components from the carousel 108. In one particular embodiment, the carousel includes a vacuum, pressure tube, and/or guide system that drops, feeds, returns, or otherwise exchanges vessels, casings, and/or tooling to the drill string 302 without requiring an arm 208 or shuttle head 310.

In alternative embodiments, the shuttle head 310 uses one or more finger grips, an electromagnetic pickup, suction, pressure, a hook, a ball joint, a mating flange, projection, recess, compression, friction, and/or other mechanical, electrical, or electromechanical enabled interface to pick up and/or drop one or more components to/from the carousel 108 or to/from the drill stick.

In various embodiments, certain technological advantages are yielded. To begin, a rig 106 can be deployed with reduced weight and/or inventory items, which can be an advantage in seafloor or cosmic body investigation where weight considerations are important. A series of carousels 108 are used to removably deliver required components in parallel, series, and/or sequentially to provide extensibility to the rig 106. Further, the rig 106 can extend to investigation depths that are deeper with a virtually limitless extensibility of a drill string 302, bound by external constraints such as motor torque. Additionally, the carousel content selection can be adjusted based on needs and requirements for a mission and can be changed or modified in an event of an unexpected circumstance. Also, the sample vessels are used to perform scientific analysis and the contents can require timely climate control for preservation. An entire carousel loaded with sample vessels can be retrieved from the rig 106 and quickly moved or stacked with another carousel inside a climate controlled container. Many other advantages are apparent in various disclosed embodiments.

Figure 10:
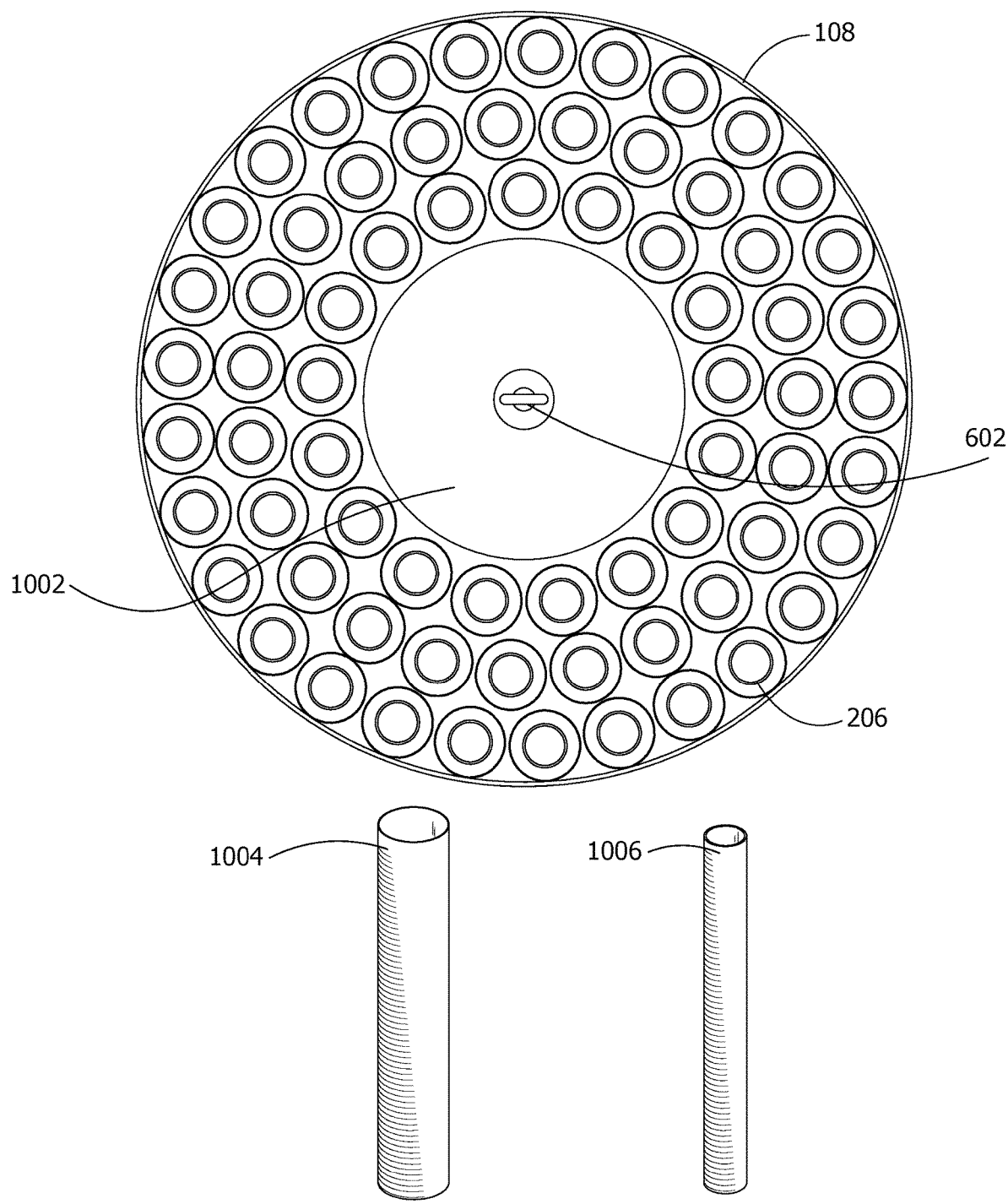
FIG. 10 is a top view of an interchangeable carousel system, in accordance with an embodiment.
Figure 11:
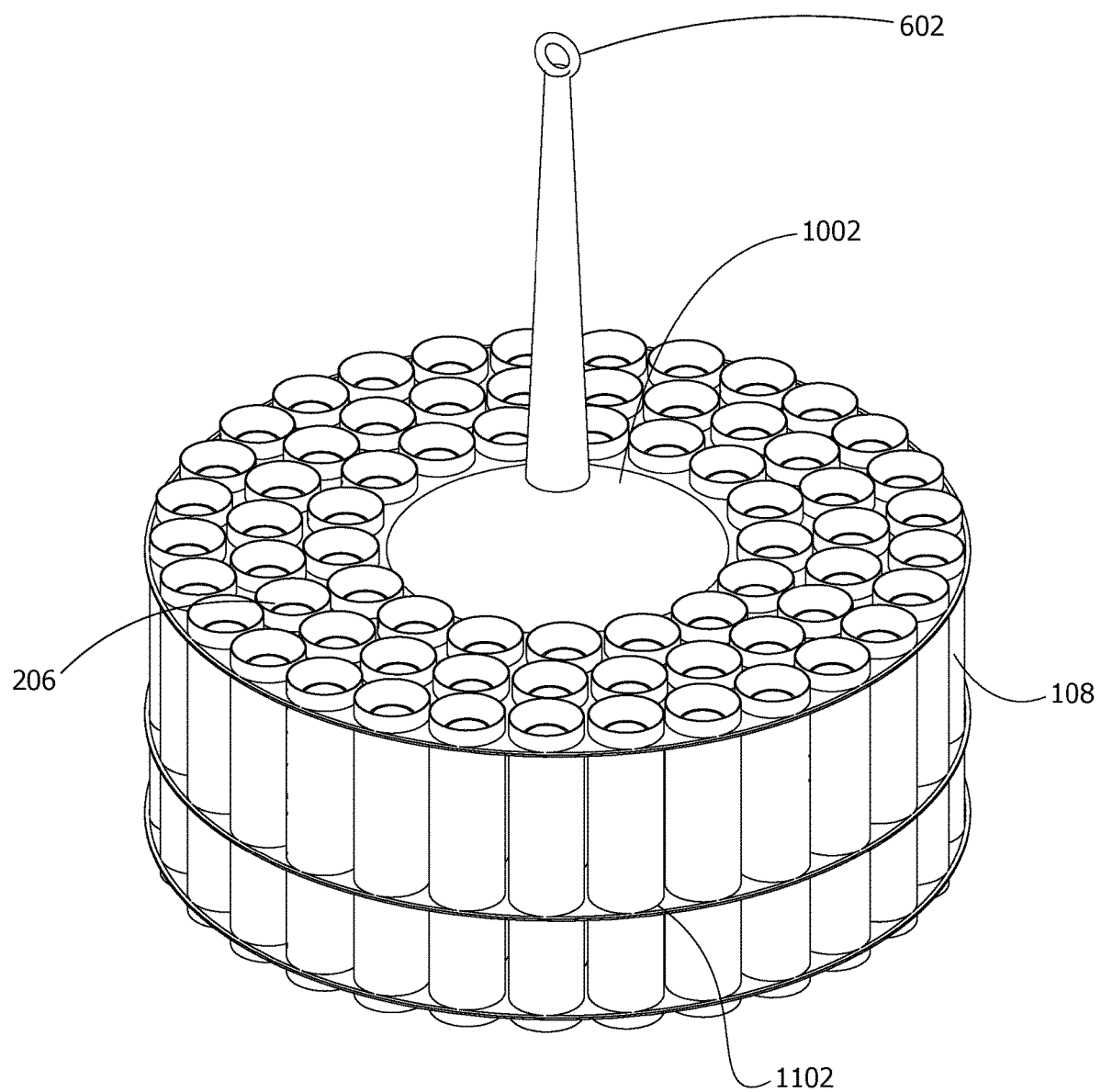
FIG. 11 is a perspective view of an interchangeable carousel system, in accordance with an embodiment.

FIGS. 10 and 11 are top and perspective views of an interchangeable carousel system, in accordance with an embodiment. In one embodiment, a carousel 108 for a geotechnical rig includes, but is not limited to, one or more addressed slots 206 to stow one or more components including at least: one or more drill casings 308, and one or more sample vessels, a funneled base configured to releasably couple to a docking station of a geotechnical rig; and a lift point 602 configured for maneuvering the carousel 108.

In one embodiment, the carousel 108 is substantially cylindrical with a central core 1002 surrounded by slots 206. The central core is approximately ⅕ to 2 meters in diameter and the slots 206 extend to a range of approximately ⅕ to 2 meters beyond the central core 1002. The carousel is approximately ⅕ to 3 meters in height. The slots 206 are rigid tubes or pipes that are approximately 2 to 6 inches in diameter and approximately 1 to 3 meters in length, such as metal tubes that are approximately 4 inches in diameter and 2 meters in length. The slots 206 are disposed in a concentric circular pattern peripheral to the inner core 1002 with approximately 1 to 5 radials of the slots 206. Many other sizes and dimensions of the carousel 108, central core 1102, or slots 206 are possible. The slots 206 can be loosely disposed within the carousel 108 and/or welded or otherwise fixedly bonded or joined to adjacent slots 206. One or more fasteners 1102 reinforce and/or retain the slots 206 from a perimeter of the carousel 108, which may include a surface with apertures for the slots 206. The slots 206 are each associated with an address, position, coordinate, or other location that is usable for selectable pickup by the rig 106 of a component therein. The slots 206 are sized and/or shaped to stow any one or more of: drill head, drill bit, diamond bit, saw tooth bit, drill stick casing 302, sample vessel, push sample, piston sample, core barrel, tube sample, vented tube, Shelby tube, non-coring assembly cap, or other tool, component, sensor, or device. The central core 1002 is constructed of metal, wood, composite, and/or other durable material to maintain the slots 206 in position, serve as a docking receptacle to the docking base 204, and/or anchor the lift point 602 for maneuvering the carousel 108. The docking receptacle is further disclosed and illustrated in FIG. 12. The lift point 602 is an eyelet, ring, hook, fastener, or other connection point that projects vertically approximately ⅓ to 3 meters to connect to a crane, ROV, guide line, or other lift device or system.

In various embodiments, the carousel 108 is cubical, rectangular, spherical, triangular, or defined by another regular or irregular shape. The carousel 108 can include a cavity center. Alternatively, the carousel 108 can include a plurality of radial arms. The shape and/or size of the carousel 108 is modifiable to suit the needs of a particular mission, rig, and/or function.

In certain embodiments, the central core 1002 is omitted and/or assumes a reduced or different profile. The central core 1002 can include a conical top that projects further to the lift point 602. Alternatively, the central core 1002 can include a substantially planar top that includes the lift point 602 directly thereon. The central core 1002 can be reduced to a dimension that supports or defines the lift point 602. Additionally, the central core 1002 can be recessed or moved to a peripheral edge of the carousel 108. In a further embodiment, the lift point 602 can retractably extend or removably attach to the carousel 108, such as to permit sleeving or stacking of the carousel 108.

In certain embodiments, the slots 206 are impressions, projections, cases, boxes, edges, or other areas to stow, deploy, receive, or otherwise provide access to the components. In certain embodiments, the slots 206 include a cap, lid, or surface that insulates, waterproofs, or otherwise protects or separates the components. The slots 206 can be rearrangeable, reconfigurable, or otherwise movable. The slots 206 are uniform in one embodiment, but in other embodiments, the slots 206 can be non-uniform with different dimensions or shapes to accommodate different components. In one particular embodiment, a slot 206 is configured to jointly stow a casing 308 and a sample vessel in a single slot 206. The slots 206 can provide access to components via a side, a top, or a bottom of the slot 206.

In one particular embodiment, the carousel 108 includes an enclosed perimeter, such as a frame and/or wall. Alternatively, the slots 206 form a perimeter edge of the carousel 108. Another configuration includes a base of the carousel 108 with a flange, lip, edge, wall, projection, or other member that extends upwards to retain or separate the slots 206. Additionally, the top surface of the carousel 108 can be open as depicted or partially enclosed with one or more apertures or openings for the slots 206.

Figure 12:
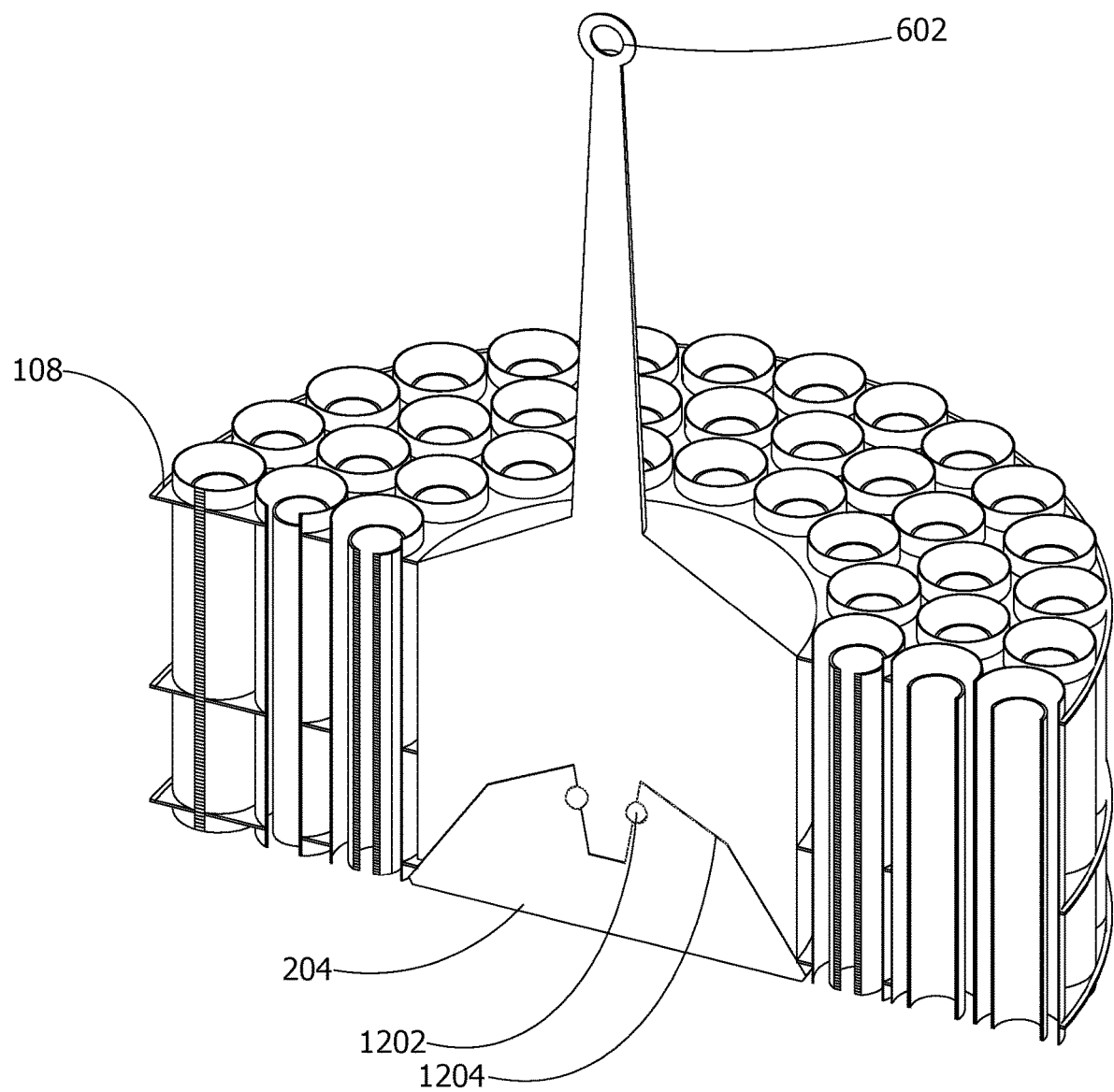
FIG. 12 is an exposed view of an interchangeable carousel system, in accordance with an embodiment.

FIG. 12 is an exposed view of an interchangeable carousel system, in accordance with an embodiment. In one embodiment, a carousel 108 for a geotechnical rig includes, but is not limited to, one or more addressed slots 206 to stow one or more components including at least: one or more drill casings 308, and one or more sample vessels, a funneled base configured to releasably couple to a docking station of a geotechnical rig; and a lift point 602 configured for maneuvering the carousel 108.

In one embodiment, the funneled base 1204 of the carousel 108 defines a concavity, recess, or other mating surface for the docking base 204 of the rig 106. The concavity of the funneled base 1204 operates to guide non-precision placement of the carousel 108 into alignment with the docking base 204 as the carousel 108 is lowered to and/or approaching the rig 106. The funneled base 1204 releasably connects with the docking base 204 in a particular rotational orientation to index the slots 206, such as using a ball and socket latching mechanism 1202 that is keyed to a particular alignment. The ball and socket latching mechanism 1202 engages to releasably lock the carousel 108 to the docking base 204 of the rig 106. Wireline intervention is used to release the ball and socket latching mechanism 1202 to separate the carousel 108 from the docking base 204.

In certain embodiments, funneled base 1204 includes one or more projections to mate with one or more recesses in the docking base 204. Alternatively, the funneled base 1204 defines a projection instead of a recess and the docking base 204 defines a recess instead of a projection. The funneled base 1204 can include a uniformly decreasing concavity diameter or one or more angular reductions in concavity diameter. The slope of the decreasing concavity diameter of the funneled base 1204 can vary or remain substantially constant. In some embodiments, the funneled base 1204 is characterized by an initial slope that transitions to a cubical, cylindrical, rectangular, or other geometrical recess.

In certain embodiments, the ball and socket mechanism 1202 is substituted or complemented with one or more other types of releasable connections. For instance, a latching mechanism, electromagnetic coupling, spring pin, or other connector is usable. The ball and socket mechanism 1202, or other releasable connection, can be released using wireline intervention techniques or using an electromagnetic, electromechanical, mechanical release that is computer operated.

In one particular embodiment, the funneled base 1204 substantially self-aligns with the docking base 204 using one or more mechanical alignment indents, detents, projections, recesses, grooves, threads, or other guides in either or both of the funneled base 1204 or the docking base 204. In certain embodiments, the carousel 108 or the docking base 204 rotates during installation of the carousel 108 to facilitate alignment engagement. In other embodiments, one or more magnets or electromagnets are incorporated in the funneled base 1204 and/or the docking base 204 to attract or repel to facilitate alignment engagement. As the carousel 108 approaches the docking base 204, the carousel 108 rotates under the magnetic force to line up the carousel 108 with the docking base 204 for matching engagement.

Figure 13:
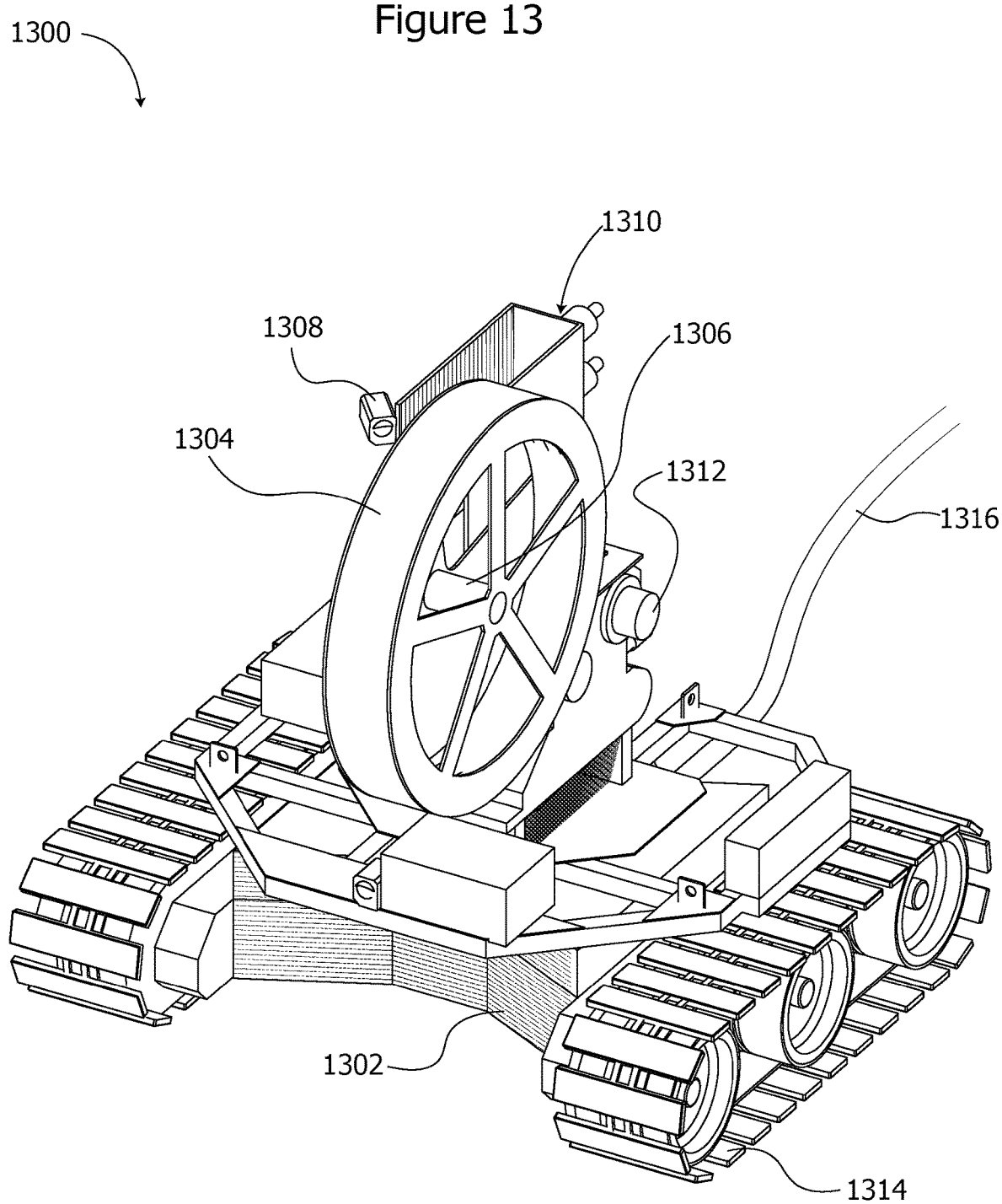
FIG. 13 is a perspective view of a cone penetration rig, in accordance with an embodiment.

FIG. 13 is a perspective view of a cone penetration rig, in accordance with an embodiment. In one embodiment, a rig for cone penetration testing 1300 includes, but is not limited to, a frame 1302; at least one cassette 1304 including at least one rotatable reel 1306; at least one sensor 1308; at least one movable roller 1310; at least one drive system 1312; and at least one tube (FIG. 14 & FIG. 15) having at least one cone penetration testing head, the at least one tube configured to be coiled about the at least one rotatable reel 1306 and extendably thrusted using the at least one drive system 1312, wherein the at least one movable roller 1310 is configured to adjust a bend radius of the at least one tube based at least partly on data received from the at least one sensor 1308.

In one embodiment, the rig 1300 is configured to perform cone penetration testing (CPT) to identify subsurface conditions in the upper approximately 100 feet of the subsurface. The rig 1300 pushes a tube having a tube sleeve and a cone (FIG. 14 & FIG. 15) into the ground. Cone penetrometer sensors disposed on the tube sleeve and/or cone are used to measure tip resistance, or the force required to push the tip of the cone, and to measure sleeve friction, or the force required to push the sleeve through the soil. A friction ratio is obtained between the sleeve friction and tip resistance, often measured as a percentage. Soil type, lithography, and/or resistance to liquefication can be inferred from these measurements. For example, the following types of soil have specific friction ratios and tip resistance profiles: sandy fill, clay, bay mud, loose sand, dense sand, or other subsurface material. Additionally, when the cone includes a seismometer, the cone can also be used to predict how local shallow soil conditions can modify shaking. The capacity of local soil conditions to modify shaking is inversely proportional to the velocity of seismic waves near the surface, which can be computed with data recorded with the seismometer. Seismic energy is created manually, such as with an air driven hammer. The time that it takes for the seismic energy to travel from the surface through the ground to the seismometer on the cone is then used to determine the distance to the seismometer. This calculation can be used to determine the average shear-wave velocity.

In certain embodiments, the rig 1300 is a terrestrial, subterrestrial, amphibious, or cosmic rig usable at a remote site such as on terrain or underwater, separated by a physical distance from a human operator. The rig 1300 can be deployed at and/or retrieved from a remote site using an onboard propulsion system and/or using assistance from an ROV, crane, guide wire, vehicle, robot, tug, tow line, or other device. The umbilical cord 1316 is configured to provide power, communication, data, and/or commands to the rig 1300. Alternatively, the rig 1300 operates in an autonomous and/or semi-autonomous mode using one or more program instructions that execute one or more operations using onboard computer circuitry. Wireless communication may optionally be used to communicate with, receive sensor data, and/or send commands to the rig 1300. The rig 1300 performs CPT functions, including using the drive 1312 to thrust the tube, cone head, and/or sleeve into the subsurface by extendably uncoiling the tube from the reel 1306 of the cassette 1304. Upon completion at one site, the rig 1300 retractably coils the tube into the reel 1306 of the cassette 1304. The rig 1300 can be repositioned to another proximate or distant site for further CPT testing, including repeating at least some of the foregoing operations. In certain embodiments, the rig 1300 can be manned or accessed by one or more human operators.

In certain embodiments, the tube is constructed of steel, metal, or other alloy. As the tube is uncoiled and recoiled during operation of the rig 1300 for CPT testing, the tube bend radius increases or otherwise changes between each cycle due to hardening of the material of the tube or other factors. The bend radius change in the tube renders coiling of the tube about the reel 1306 within the cassette 1304 more difficult or impossible. Accordingly, the sensor 1308 monitors the bend radius change of the tube and the movable roller 1310 applies targeted force to the tube to correct deviations in the bend radius to maintain a desired bend rate and/or maintain a consistent diameter. The process of monitoring the bend radius of the tube and adjusting the bend radius is continued until such time as the tube is fatigued and/or unusable.

In some embodiments, the cassette 1304 is approximately 1 to 5 meters in diameter and approximately ⅓ to 1 meter in width, although other dimensions of cassette 1304 can be employed. The cassette 1304 can be fully or partly enclosed, such as using a shell, casing, or permitter wall. The reel 1306 rotates within or relative to the cassette 1304. However, in certain embodiments, the cassette 1304 is omitted in favor of an exposed reel 1306. The cassette 1304 is optionally removable and/or exchangeable with another cassette 1304, such as to enable replacement or exchange of a fatigued or consumed CPT tube or cone penetration head.

In certain embodiments, the at least one cassette 1304 includes at least one motor to facilitate retraction and/or extension of the at least one tube relative to the at least one rotatable reel 1306. The drive 1312 can operate to coil and uncoil the tube in the cassette 1304 by pulling or pushing the tube. The reel 1306 can spin or rotate substantially freely and/or through the thrusting and/or retraction caused by the drive 1312. Alternatively, a separate motor or rotational drive system can assist or supplement the coiling or uncoiling of the tube by forcibly rotating the reel 1306 in a clockwise and/or counterclockwise direction.

In other embodiments, the umbilical cord 1316 is optional and/or replaced or complimented with a wireless communication interface, computer readable storage media with a computer program executable on one or more processors, a battery, a motor, an engine, or other alternative component.

In one particular embodiment, the rig 1300 includes at least one continuous track propulsion system 1314. The continuous track propulsion system 1314 is composed of one or more wheels and a track, which one or more wheels are driven by an electric, gasoline, diesel, or other motor or engine. The propulsion system 1314 can optionally include one or more tires, wheels, legs, robotic limbs, ballasts, jets, or other system that propels or otherwise moves the rig 1300. The propulsion system 1314 can be omitted with the rig 1300 resting directly or indirectly on a surface.

Figure 14:
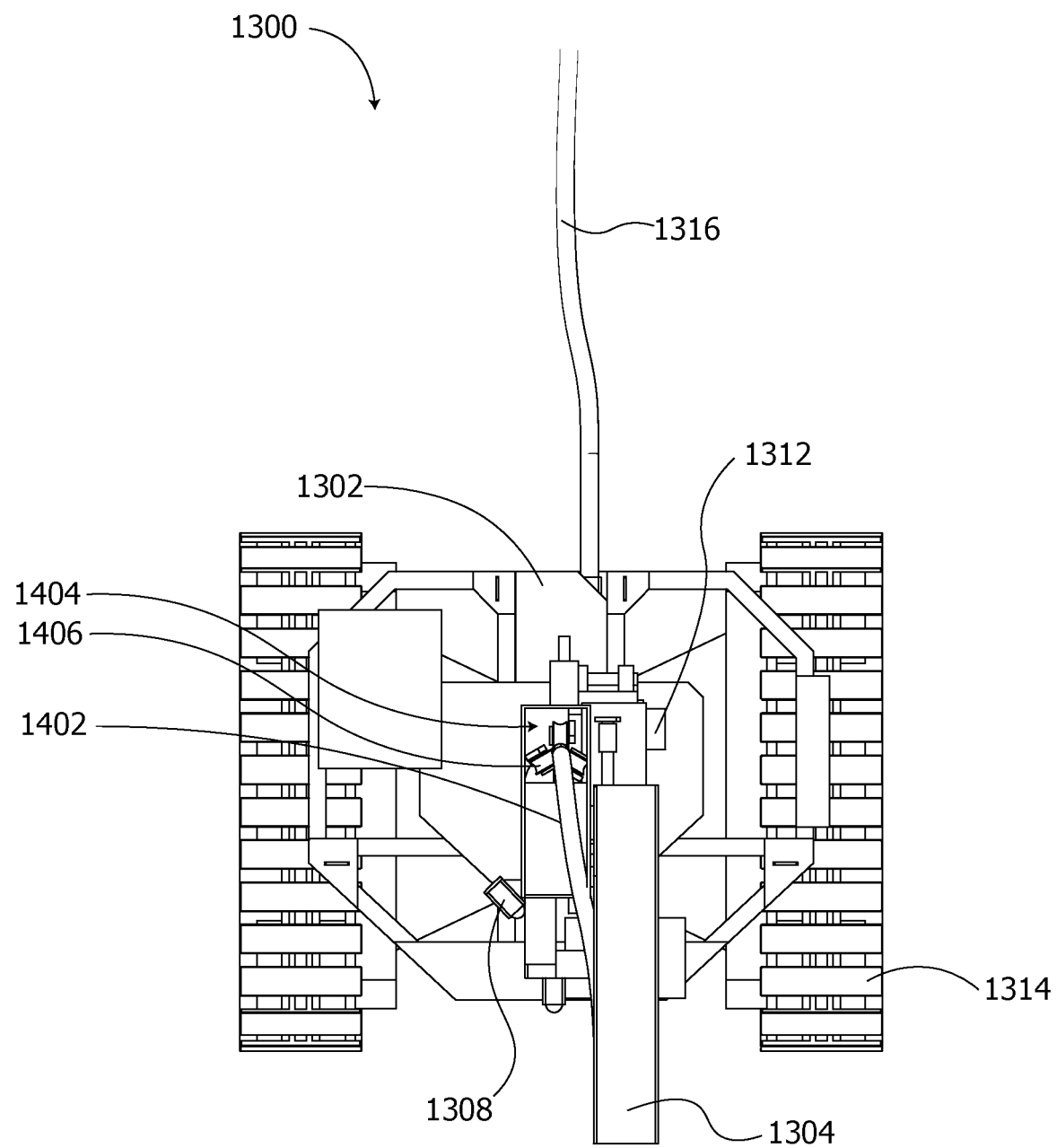
FIG. 14 is a top view of a cone penetration rig, in accordance with an embodiment.

FIG. 14 is a top view of a cone penetration rig, in accordance with an embodiment. In one embodiment, a rig 1300 for cone penetration testing includes, but is not limited to, a frame 1302; at least one cassette 1304 including at least one rotatable reel; at least one sensor 1308; at least one movable roller 1406; at least one drive system 1312; and at least one tube 1402 having at least one cone penetration testing head, the at least one tube 1402 configured to be coiled about the at least one rotatable reel and extendably thrusted using the at least one drive system 1312, wherein the at least one movable roller 1406 is configured to adjust a bend radius of the at least one tube 1402 based at least partly on data received from the at least one sensor 1308. In a further embodiment, a cone penetration testing system 1300 includes, but is not limited to, a frame 1302; at least one rotatable reel 1306; at least one movable roller 1406; and at least one sensor 1308, wherein the at least one movable roller 1406 is configured to adjust a bend radius of at least one tube 1402 coiled about the at least one rotatable reel 1306 based at least partly on data received from the at least one sensor 1308.

In one particular embodiment, the tube is a steel tube of approximately 1 inch to 6 inches in diameter, such as 2 inches. The tube 1402 is thrust substantially downward via the drive channel 1404 by the drive system 1312. As the tube 1402 is thrust by the drive system 1312, the tube 1402 is uncoiled from the cassette and/or rotatable reel 1306. The tube 1402 includes one or more sensors; for example, the tube 1402 can include one or more cone penetrometers and/or one or more seismometers in association with one or more power, data, or analog output wires. The tube 1402 is pushed into the subsurface to one or more depths consistent with a particular mission and uncoiled from the cassette and/or rotatable reel 1306 to accommodate the cone penetration operations. Upon completion, the drive system 1312 reverses and/or retracts the tube 1402, which is recoiled into the cassette 1304 and/or rotatable reel 1306. The tube 1402 passes along the at least one movable roller 1406 between the drive system 1312 and the cassette and/or rotatable reel 1306. The at least one movable roller 1406 is configured to move, shift, press, release, retract, rotate, advance, spin, or otherwise change position relative to the tube 1402 in order to effectuate a desired curvature on the tube 1402. The sensor 1308 includes a camera, video recorder, and/or other imager that is operable to capture, communicate, record, measure, or otherwise provide one or more images of the tube 1402 as the tube 1402 enters the cassette and/or rotatable reel 1306. Imagery from the sensor 1308 is output, processed, and/or otherwise analyzed to determine a need for and/or a degree of curvature correction required to spool the tube 1402 within the cassette and/or rotatable reel 1306. A processor controls one or more transistors and/or a hydraulic system or electric motor to adjust the movable roller 1406 based on any curvature requirements detected or determined using information from the sensor 1308. The curvature adjustment provides a requisite bend radius in the tube 1402 to return the tube 1402 back into the cassette 1304, thereby overcoming or correcting deformation and/or fatigue in the tube resulting from uncoiling, coiling, and/or thrusting into the subsurface.

In other embodiments, the drive system 1312 is hydraulic, engine-driven, and/or electric-based. The drive system 1312 can include a track, roller, or other friction-based system to force, thrust, or otherwise deploy the tube 1402 downward to and/or into a subsurface. The drive system 1312 may include a rotational motor, engine, or hydraulic system for forcibly turning the rotatable reel 1306 to support or facilitate extension of the tube 1402. Power for the drive system 1312 may be provided remotely via the umbilical cord 1316 or using an onboard fuel system or battery.

In some embodiments, the drive channel 1404 is offset and/or adjacent to the cassette and/or rotatable reel 1306 as depicted. The tube 1402 exits the cassette and/or rotatable reel 1306 on one side and passes through the drive channel 1404 to the surface and/or subsurface. The drive channel 1404 in this embodiment can be offset to a left or right side of the cassette and/or rotatable reel 1306. In another embodiment, the drive channel 1404 is positioned inline with the cassette and/or rotatable reel 1306 such that the tube 1402 is configured to pass through the drive channel 1404 without being substantially offset. The cassette and/or rotatable reel 1306 may include a partial or completely open perimeter wall or side wall to facilitate ingress and/or egress of the tube 1402 from the cassette and/or rotatable reel 1306.

In certain embodiments, the sensor 1308 is differently positioned and/or oriented. For instance, the sensor 1308 can be oriented with a field of view toward the passageway for the tube 1402 in the cassette and/or rotatable reel 1306. Alternatively, the sensor 1308 can be oriented with a field of view toward the movable roller 1406 and/or the drive channel 1404. Additionally, the sensor 1308 can be oriented with a field of view toward the inside of the cassette and/or rotatable reel 1306. The sensor 1308 can be positioned at or proximate to any of the drive channel 1404, the cassette 1304, the movable roller 1406, and/or the tube 1402. In certain embodiments, the sensor 1308 is movable and/or rotatable about one, two, three, or more axis. In other embodiments, a plurality of sensors 1308 are arranged proximate to and/or with fields of view of any of the drive channel 1404, the movable roller 1406, the cassette and/or rotatable reel 1306, the drive system 1312, and/or the tube 1402.

Figure 15:
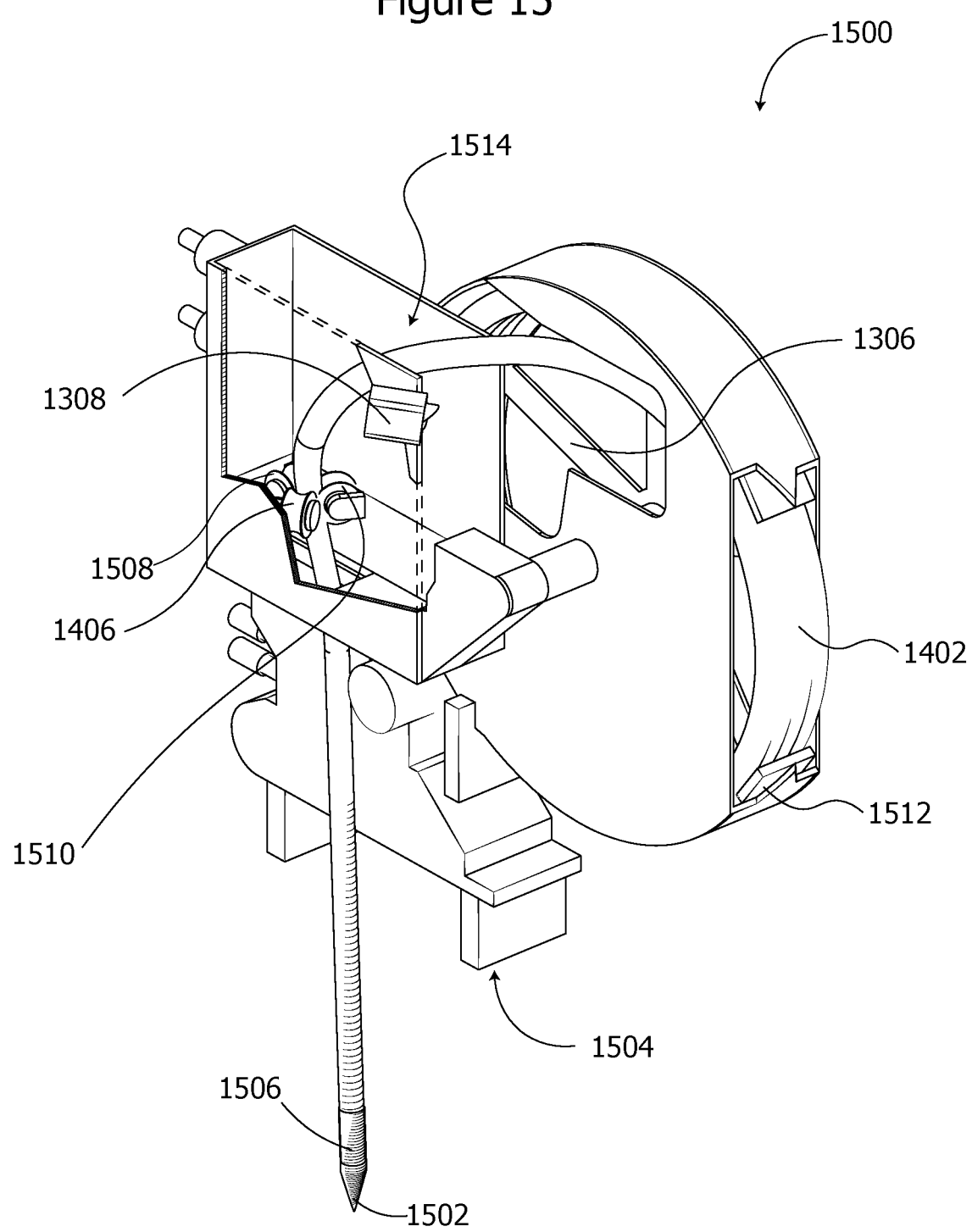
FIG. 15 is a perspective partially exposed view of a cassette reel system for a cone penetration rig, in accordance with an embodiment.

FIG. 15 is a perspective partially exposed view of a cassette reel system for a cone penetration rig, in accordance with an embodiment. In one embodiment, a cassette system for cone penetration testing includes, but is not limited to, at least one rotatable reel 1306; at least one sensor 1308; and at least one movable roller 1406; wherein the at least one movable roller 1406 is configured to adjust a bend radius of at least one tube 1402 coiled about the at least one rotatable reel 1306 based at least partly on data received from the at least one sensor 1308. The tube 1402 includes a cone penetration sleeve 1506 with a cone head 1502. In one particular embodiment, the cone head 1502 and/or the cone penetration sleeve 1506 is replaceable on the tube 1402.

Figure 16:
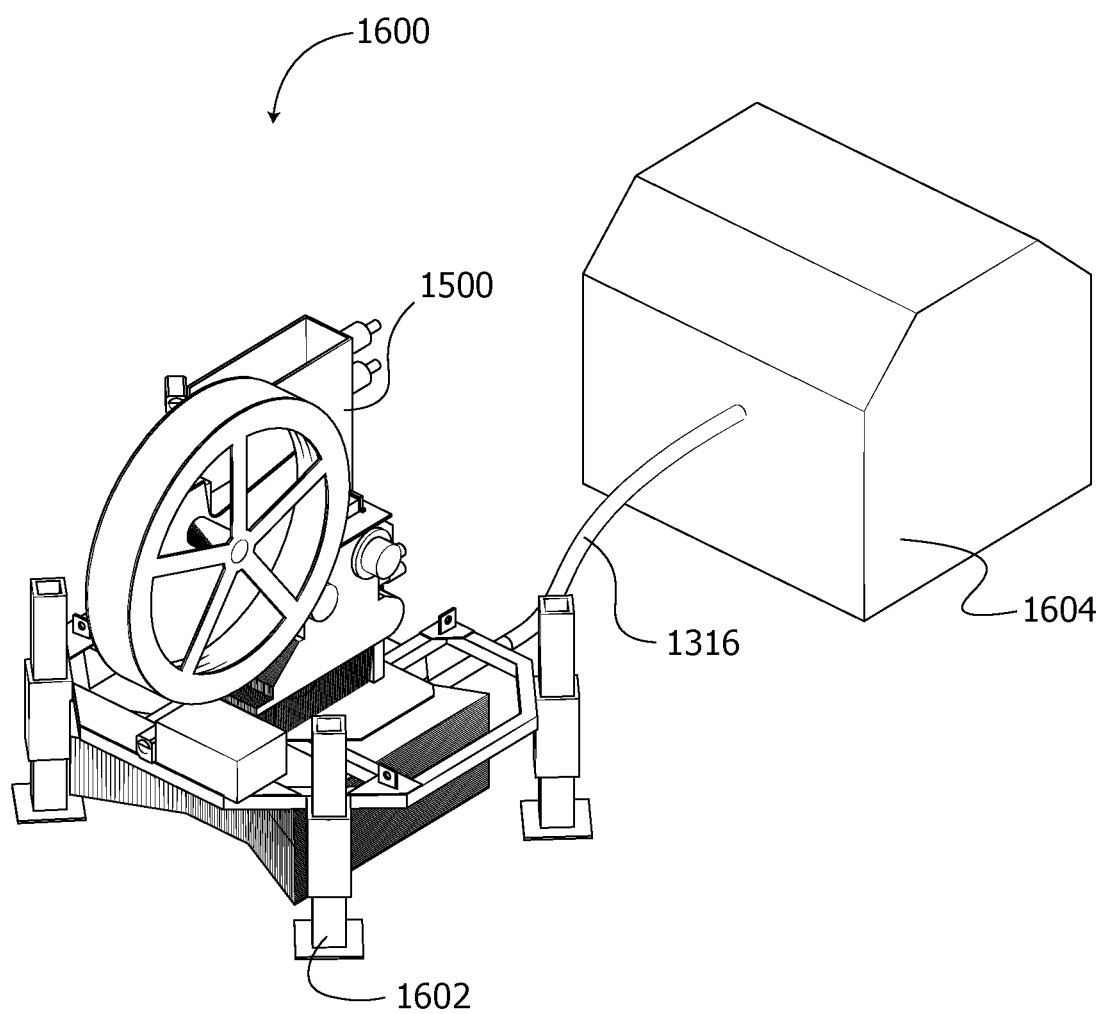
FIG. 16 is a perspective view of a cone penetration rig, in accordance with an embodiment.

In one embodiment, the cassette 1500 is removably installable on the rig (FIGS. 13, 14, & 16). The cassette 1500 includes a docking base 1504 that releasably locks with one or more mating structures and/or associated fasteners of the frame of the rig. The cassette 1500 can be installed to the rig to enable CPT testing and/or investigation using the tube 1402 and its associated cone penetration sleeve 1506 and cone head 1502. The tube 1402 is extendable from the rotatable reel 1306 and retractable into the rotatable reel 1306 for a plurality of cycles. After a specified number of cycles or upon a detected fracture, irregularity, or other deformity, the cassette 1500 can be removed from the rig and replaced with another cassette 1500. The replacement cassette 1500 can include a replacement tube 1402 that enables continued operation of the rig for testing and/or investigation. In one particular embodiment, the rig or frame includes a funnel mount with a conical head to guidably receive the docking base 1504. Locking bearings or a pin are engaged and/or removed using one or more techniques such as guidewire intervention, electromagnetic release, and/or computer control. In one particular embodiment, the docking base 1504, the rig, or the frame includes a magnet or electromagnet to facilitate alignment and coupling of the cassette 1500.

In a further embodiment, the rotatable reel 1306 is removably mounted with the cassette 1500. Thus, the rotatable reel 1306 can be mounted on the cassette to enable repeated cycles of extension and/or retraction of the tube 1402. Upon reaching a specified number of cycles or upon a detected fracture, irregularity, or other deformity, the rotatable reel 1306 can be removed from the cassette 1500 and another rotatable reel 1306 with a replacement tube 1402 can be loaded onto the cassette 1500. The replacement rotatable reel 1306 with the replacement tube 1402 enables continued operation of the cassette 1500 for testing and/or investigation. In certain embodiments, the cassette 1500 includes a funnel mount with a conical head that is configured to guidably receive the rotatable reel 1306 into position. Locking bearings or a pin are engaged and removed using one or more techniques such as guidewire intervention, electromagnetic release, and/or computer control. In one particular embodiment, the rotatable reel 1306 or the cassette 1500 includes a magnet or electromagnet to facilitate alignment and/or coupling to the cassette 1500.

In a further embodiment, the at least one cassette 1500 includes a guide channel 1514 to facilitate retraction and/or extension of the at least one tube 1402 relative to the at least one rotatable reel 1306. The guide channel 1514 can consist of an opening, surface, edge, curvature, angled wall, or other structure that supports and/or directs the tube 1402 to or from the rotatable reel 1306. In one particular embodiment the guide channel 1514 includes one or more rollers or bearings configured to reduce friction of the tube 1402 against any surface of the guide channel 1514. In another embodiment, the guide channel 1514 can consist or incorporate any of rubber, plastic, metal, or other material that reduces friction of the tube 1402 against any surface of the guide channel 1514. In certain embodiments, the guide channel 1514 includes a movable guide that facilitates placement of the tube 1402 on a spool line within the rotatable reel 1306. In some embodiments, the rotatable reel 1306 is positioned inline with the guide channel 1514 so as to occupy substantially the same plane or can be positioned offset from the guide channel 1514 as depicted.

In one embodiment, the sensor 1308 is configured to sample, measure, obtain, determine, or detect information on movement, position, shape, and/or pressure associated with the tube 1402, such as with sensors 1512 positioned in a perimeter or circumference wall of the cassette 1500. One or more computer processors use information obtained from the sensor 1308 to determine a deviation from a desired bend radius in the tube 1402. The one or more computer processors is further configured to automatically determine a position of the at least one movable roller 1406 to correct the deviation from the desired bend radius in the tube 1402 and return the tube 1402 to the desired bend radius. For instance, as the tube 1402 is recoiled, the bend radius may increase due to fatigue in the metal of the tube 1402. The sensor 1308 is used by the processor to calculate a movement of the roller 1406 that will tighten the bend radius of the tube 1402 as the tube 1402 is retracted into the rotatable reel 1306. The processor can implement the movement by controlling circuitry and/or a motor associated with the roller 1406. Feedback information is obtained by the processor using the sensor 1308 to determine any position changes of the roller 1406 that are required to maintain the desired bend radius of the tube 1402. The processor can continuously receive information from the sensor 1308 and make adjustments to positioning of the roller 1406 to maintain the bend radius within a certain tolerance. In an event that the desired bend radius cannot be maintained within a desired tolerance level, the processor can control a drive system to discontinue coiling or extend the tube 1402.

In certain embodiments, the sensor 1308 consists of a camera that captures one or more of still images, infrared images, videos, or other radiofrequency information. The sensor 1308 can alternatively include a proximity sensor that is usable to detect whether the tube 1402 is within or outside a particular distance range or position range. Optionally, the sensor 1308 can include a contact sensor that is usable to detect physical touching of the tube 1402 with a surface. The sensor 1308 can include any one or more of the foregoing or other type of sensor, including a combination of sensor types that operate together to obtain information usable by one or more processors to determine or recognize fatigue, bend radius, and/or deformation information associated with the tube 1402.

In one embodiment, the movable roller 1406 further includes an idler roller 1508. The movable roller 1406 pivots, shifts, rotates, or otherwise moves relative to the tube 1402 and the idler roller 1508. The idler roller 1508 is configured to provide a backstop to the movable roller 1406 while enabling rollable passing of the tube 1402. Together, the movable roller 1406 and the idler roller 1508 operate in coordination to produce a desired bend radius, conformance, and/or curvature of the tube 1402. For instance, the movable roller 1406 can press the tube 1402 at a point above the idler roller 1508 while the tube 1402 rolls through the movable roller 1406 and the idler roller 1508 enroute to the rotatable reel 1306, thereby shortening the bend radius of the tube 1402. Alternatively, the movable roller 1406 can press the tube 1402 at a point below the idler roller 1508 while the tube 1402 rolls through the movable roller 1406 and the idler roller 1508 enroute to the rotatable reel 1306, thereby increasing the bend radius of the tube 1402. The movable roller 1406 can shift up, down, in, out, around, and/or side to side to in various degrees relative to the idler roller 1508, with or without pivoting, to produce the desired bend radius, curvature, or conformance in the tube 1402.

In one particular embodiment, the cassette 1500 further includes at least one additional movable roller 1510 that operates in conjunction with the movable roller 1406. The movable roller 1406 and movable roller 1510 operate in coordination to effect a desired bend radius, conformance, or curvature in the tube 1402 similar to use of the idler roller 1508. However, with the additional movable roller 1510, an additional degree of precision with conformance can be achieved. For instance, beyond effecting a bend radius or curvature change, the movable roller 1406 and movable roller 1510 can also more effectively address deformations and/or other defects by the following independent movements: up, down, side to side, in, out, swivel, rotate, pivot, and/or other maneuver relative to one another. In certain embodiments, an idler roller 1508 is present in conjunction with the movable roller 1510 and the movable roller 1406. For instance, one movable roller 1406 can operate below the idler roller 1508 and the other movable roller 1510 can operate above the idler roller 1508. By independently moving either the movable roller 1510 or the movable roller 1406 against, away, or around the tube 1402 as the tube 1402 traverses the same, desired conformances, bend radiuses, curvatures, conformances, and/or adjustments can be effected.

While the movable roller 1406 and/or the movable roller 1510 have been discussed in reference to adjusting or correcting curvature or bend radius upon retraction, the movable roller 1406 and/or the movable roller 1510 may also operate to effect straightening of the tube 1402 upon extraction to enable downward thrusting of the tube 1402. The sensor 1308 or another sensor is configured to obtain information regarding the linearity of the tube 1402 as it exits the guide channel 1514 and/or the cassette 1500. Any non-linearity of the tube 1402 can be corrected via movement of either the movable roller 1406 and/or the movable roller 1510, with or without the idler roller 1508. The degree, position, orientation, and rotation of either the movable roller 1406 and/or the movable roller 1510 can be adjusted to effect the desired shape of the tube 1402 as it progresses toward the surface and/or into the subsurface. Thus, conformance, alignment, shape bending, radius, curvature, linearity, or other features can be corrected, induced, or maintained during either retraction and/or extraction using the movable roller 1406 and/or the movable roller 1510, with or without an idler roller 1508.

In certain embodiments, the movable roller 1406 and/or the movable roller 1510 operate with a hydraulic system, electric motor, or engine that pushes or releases based on one more user inputs or in response to processor control. The hydraulic system, electric motor, or engine is controlled by a processor and associated circuitry via user commands, program instructions, artificial intelligence, machine learning, and/or sensor input. In one particular embodiment, a radius control system is provided that operates the hydraulic system, electric motor, or engine to maintain the bend radius of the tube 1402 to substantially match the curvature of the rotatable reel 1306 at the current spool level. The tube 1402 coils upon itself beginning from an inner level of the reel 1306 and progressing to an outer level of the reel 1306. Each progressive level of the tube 1402 on the reel has a larger bend radius. Thus, the radius control system can dynamically adjust the bend radius of the tube 1402 as it retracts to substantially match the current spool level within the reel 1306. Beginning at a smaller bend radius, the radius control system can increase the bend radius of the tube 1402 based on the level within the rotatable reel 1306.

In certain embodiments, the radius control system determines a current level of the tube 1402 within the reel 1306, detects a bend radius of the tube 1402, determines a desired curvature for a current portion of the tube 1402, and/or obtains feedback regarding the fit or shape of the tube 1402 within the reel 1306, at least partly using information obtained from the sensor. The radius control system is configured to control at least one hydraulic system, electric motor, or engine to change a position of the at least one movable roller 1406 relative to the at least one tube 1402 based at least partly on a current level of the tube 1402 within the reel 1306, a bend radius of the tube 1402, a desired curvature for a current portion of the tube 1402, and/or feedback regarding the fit or shape of the tube 1402 within the reel 1306. Optionally, user input may be provided to override, set, adjust, improve, and/or otherwise influence a position of the at least one movable roller 1406 relative to the at least one tube 1402. For example, the radius control system can detect that the tube 1402 is currently spooling on level 2, requiring, for example, a 1 meter bend radius. The radius control system can determine that the current portion of the tube 1402 has a 1.1 meter bend radius as the tube 1402 exits the movable roller 1406 and the idler roller 1508. The radius control system can then controllably adjust a position of the movable roller 1406 to apply increased pressure against the tube 1402, for example by moving toward the tube 1402 an additional 3 cm. As the tube 1402 progresses further, the radius control system can evaluate the bend radius of the tube 1402 and, upon determining that a correction is required, make an incremental adjustment to the position of the movable roller 1406, such as by backing off the tube pressure by 0.5 cm. Machine learning can be applied to improve operation of the radius control system. The bend radius and position change amounts will be dictated by the particular dimensions of the cassette 1500 and associated components and will change based at least upon cycle number of the tube 1402 and/or the type of material used for the tube 1402, but they provide an example of the dynamic and continuous operation of the radius control system.

In certain embodiments, a hydraulic leak detector is provided to measure the level of hydraulic fluid in the system. Should the level drop below a specified threshold or become empty, an output signal or alert can be provided and/or an automated action can be performed.

In other embodiments, the positions of the movable roller 1406, the movable roller 1510, or the idler roller 1508 are changeable. There may be additional or fewer idler rollers or movable rollers. Also, feed or exit rollers, channels, tubes, guides, or tracks may be implemented to further support a desired shape of the tube 1402.

FIG. 16 is a perspective view of a cone penetration rig, in accordance with an embodiment. In one embodiment, a rig 1600 for cone penetration testing includes, but is not limited to, a cassette 1500 supported by a structure and/or deck with one or more support legs 1602. An umbilical cord 1316 links the rig 1600 with a control unit 1604. The rig 1600 is configured to provide terrestrial, subterrestrial, or cosmic soil investigation and/or analysis, such as on land or on a seafloor surface.

In certain embodiments, the one or more support legs 1602 include a plurality of legs 1602 that are independently height adjustable to accommodate surface irregularities or sloping terrain. Thus, the support legs 1602 can be extended or retracted as required to maintain or situate the rig 1600 in an orientation such that the cone penetration tube is deployed in a substantially perpendicular manner into the Earth or other cosmic body. Any of the support legs 1602 can include pivot or swivel bases, articulating joints, and/or anchor points. The support legs 1602 can be manually adjusted and/or be driven by one or more hydraulic systems, electric motors, and/or engines, any of which can be user-controlled or controlled using a processor and/or circuitry. In one particular embodiment, a level sensor is situated on the rig 1600 and a processor samples information from the level sensor to determine control instructions for a hydraulic system that actuates the support legs 1602 in order to automatically level the rig 1600.

In a further embodiment, the control unit 1604 provides one or more of power, communication, data, and/or control instructions to or from the rig 1600 via the umbilical cord 1316. While the control unit 1604 is illustrated in proximity to the rig 1600, the umbilical cord 1316 may stretch for many feet or miles to a control unit 1604 that is more remote from the rig 1600. In the case of power, the umbilical cord 1316 can be omitted with a battery or fuel supply situated on or with the rig 1600. Optionally, any communication, control, or data functions of umbilical cord 1316 be implemented using wireless communication, including cellular, radio, WIFI, satellite, BLE, BLUETOOTH, and/or beacon technology. On one particular embodiment, the control unit 1604 includes a plurality of umbilical cords that each are associated with a different rig, thereby enabling a centralized hub and spoke system to a plurality of rigs that are independently conducting soil investigation and/or testing at different sites. In another embodiment, the control unit 1604 is incorporated on or within a vehicle, vessel, dwelling, or other structure.

Figure 17:
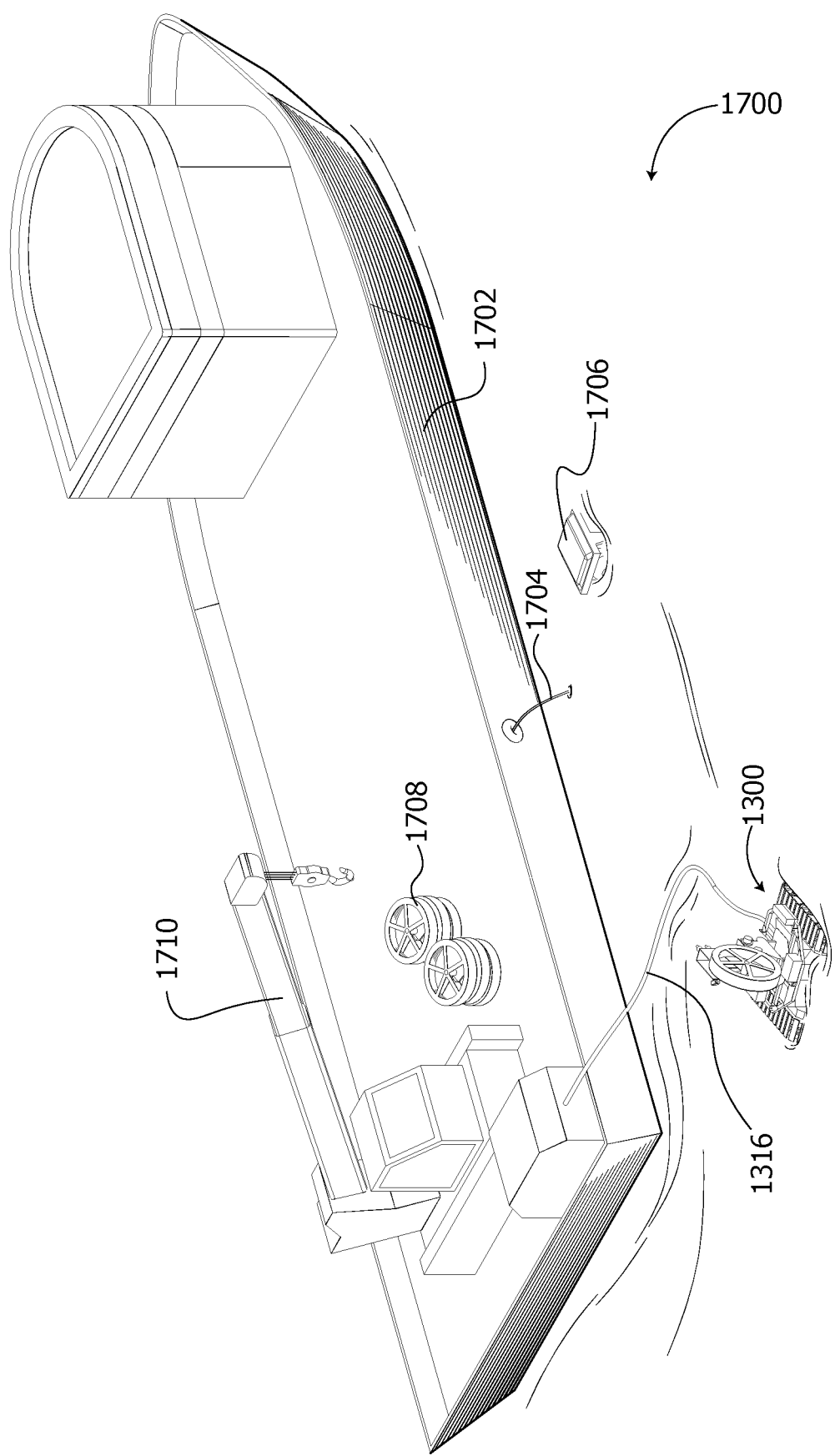
FIG. 17 is a perspective view of a vessel with a cone penetration rig, in accordance with an embodiment.

FIG. 17 is a perspective view of a vessel system with a cone penetration rig, in accordance with an embodiment. In one embodiment, the vessel system 1700 includes, but is not limited to, a vessel 1702 and a rig 1300. The vessel 1702 includes a crane 1710 that is operable to lower, raise, or otherwise maneuver the rig 1300. An ROV 1706 is operable to guide the rig 1300 using one or more guide wires 1704. An umbilical cord 1316 links the rig 1300 with the vessel 1702. One or more exchangeable and/or replacement cassettes 1708 are stowable on or with the vessel 1702 and deployable to the rig 1300 using the crane 1710 and/or ROV 1706. Accordingly, the vessel system 1700 enables remote testing and/or soil investigation in sea, ocean, lake, or other water covered locations.

In one embodiment, the vessel 1702 is a barge, ship, boat, platform, floating rig, and/or other similar surface or subsurface situated vessel. The vessel 1702 includes at least one crane 1710, which is a mechanically, electrically, electromechanically, and/or engine or motor driven device for lifting, moving, lowering, or otherwise maneuvering one or more objects, including the one or more cassettes 1708, the rig 1300, and/or an ROV 1706.

In one embodiment, the vessel 1702 transports the one or more cassettes 1708, the rig 1300, and/or the ROV 1706 to a desired location in an ocean, sea, lake, or other body of water, whereby the crane 1710 deploys the rig 1300 and/or the ROV 1706 into the water. One of the cassettes 1708 can be deployed with the rig 1300 or separately from the rig 1300. The ROV 1706 assists in the movement and/or positioning of the rig 1300 from the vessel 1702 to a seafloor, such as by using a guidewire 1704 and heave compensation systems. The one or more cassettes 1708 can be transitioned from the vessel 1702 to the rig 1300 or from the rig 1300 to the vessel 1702 using the ROV 1706, the guide wire 1704, and/or and the crane 1710. The one or more cassettes 1708 each include a spooled CPT tubing, sleeve, and cone penetration head. Therefore, the rig 1300 can one cassette 1708 on the seafloor for purposes of soil investigation and/or analysis and the one cassette 1708 can be interchanged with one or more additional cassettes 1708 from the vessel 1702 to extend the lifespan of the rig 1300 on the seafloor, for example. While on the vessel 1702, the cassettes 1708 are stackable on a deck, stowage compartment, or other unit, either before or after deployment on the rig 1300. Any of the foregoing operations can be under complete or partial autonomous control using a computer system, circuitry, and/or associated programming. Alternatively, some or all of the operations can be manually effectuated or assisted.

The vessel 1702 is illustrated as a water-based vessel for example purposes only, but the vessel 1702 can be any device or system usable to deliver the rig 1300 and/or one or more cassettes 1708 to a desired terrestrial and/or subterrestrial location. In other embodiments, the rig 1300 can position itself in any terrestrial and/or subterrestrial environment independent of the vessel 1702. In the embodiment where the vessel 1702 comprises a ship, the vessel 1702 can include a 120 ft work vessel with approximately 20 anchors and the crane 1720, operating to approximately 2-3 k meters depth.

In a further embodiment, the rig 1300 comprises a cone penetration testing (CPT) rig that remotely operates on or below a terrestrial or subterrestrial surface, such as a seafloor and/or subseafloor. The rig 1300 can include propulsion systems to facilitate independent movement or positioning. Alternatively, the rig 1300 can be moved or positioned entirely or partly by another system or device, such as the ROV 1706.

In certain embodiments, the rig 1300 is at least partly enabled using the one or more cassettes 1708 that are interchangeably coupled to the rig 1300, which can be independently deployed to the rig 1300 and/or retrieved from the rig 1300 as needed or required. Thus, the rig 1300 can launch independently of any of the cassettes 1708 or with one cassette 1708 initially present. The rig 1300 deploys the tubing, sleeve, and/or cone penetration head from one of the cassettes 1708 to provide sampling and/or investigation at a series of soil depths. The cassette 1708 can be removed from the rig 1300 and an additional cassette 1708 can be installed on the rig 1300. The extensibility of the rig 1300 is therefore provided.

In one embodiment, the ROV 1706 transports the cassettes 1708 from the vessel 1702 to the rig 1300. The ROV 1706 attaches to a lift point on the cassette 1708 using assistance from the crane 1710 and guides the cassette 1708 to the rig 1300. The ROV 1706 can be any robot or remote/automated controllable device, such as a LARS. However, it is contemplated that the one or more cassettes 1708 can be self-guided under independent propulsion to and/or from the rig 1300 without requiring use of the ROV 1706. Alternatively, the crane 1710 or guide wire 1704 can optionally be used to transport the one or more cassettes 1708 to and/or from the rig 1300. In certain embodiments, the ROV 1706 is a terrestrial vehicle or system that delivers and retrieves the one or more cassettes 1708 between a staging location and the rig 1300. The staging location can include a vehicle, platform, container, climate-controlled unit, refrigeration unit, or the like. For instance, the rig 1300 can be deployed to a mine or tunnel location and the ROV 1706 can run exchanges of the cassettes 1708 from a staging location at or proximate to a mine entrance.

In certain embodiments, the one or more cassettes 1708 are staged or stored on a deck or surface area of the vessel 1702. Optionally, one area of the deck or surface area of the vessel 1702 is used for one or more cassettes 1708 ready for deployment to the rig 1300 and a different area of the deck or surface area of the vessel 102 is used for one or more cassettes 1708 that have been returned from the rig 1300. The cassettes 1708 are configured to be stackable with one another to conserve staging and/or storage space. For instance, the cassettes 1708 can include a flat bottom surface area that rests upon another of the cassettes 1708. Alternatively, a male/female mechanical coupling can be provided between adjacent cassettes 1708 to limit or prevent movement or shifting. Additionally, the center portions of the cassettes 1708 can operate in conjunction with one another to define a space for containing a stacked cassette 1708, such as in a pyramid type arrangement. The cassettes 1708 can be stacked without substantial limitation and may be confined using one or more frames to prevent or limit movement or shifting.

The vessel system 1700 is exemplary and can be configured in a variety of ways. The crane 1710 can be omitted or substituted with another lifting or hoist mechanism. The crane 1700 can be movable and/or differently located on the vessel 102. Likewise, it is contemplated that a plurality of cranes 1710 can be utilized for backup redundancy or to increase efficiency. Multiple rigs 1300 and/or ROVs 1706 can also be utilized to enable backup redundancy or to increase efficiency, such as by enabling simultaneous sampling and investigation operations at one or more different sites. Optionally, the cassettes 1708 may be non-interchangeable and the rig 1300 may include a dedicated cassette 1708.

The present invention may have additional embodiments, may be practiced without one or more of the details described for any particular described embodiment, or may have any detail described for one particular embodiment practiced with any other detail described for another embodiment.

While preferred and alternate embodiments of the invention have been illustrated and described, as noted above, many changes can be made without departing from the spirit and scope of the invention. Accordingly, the scope of the invention is not limited by the disclosure of these preferred and alternate embodiments. Instead, the invention should be determined entirely by reference to the claims that follow.

What is claimed is:

1. A rig for cone penetration testing, the rig comprising:
   a frame;
   at least one cassette including:
      at least one rotatable reel that rotates within the at least one cassette;
      at least one tube having a cone penetration testing head, the at least one tube being coiled about the at least one rotatable reel within the at least one cassette; and
      at least one docking base that releasably engages one or more mating structures on the frame;
   at least one sensor;
   at least one movable roller; and
   at least one drive system configured to extend or retract the at least one tube from the at least one cassette,
   wherein the at least one movable roller is configured to adjust a bend radius of the at least one tube based at least partly on data received from the at least one sensor.

2. The rig of claim 1, further comprising:
   at least one continuous track propulsion system.

3. The rig of claim 1, further comprising:
an umbilical cord.

4. The rig of claim 1, wherein the at least one cassette is removable.

5. The rig of claim 1, wherein the frame further comprises a funnel mount, the funnel mount configured to guide the at least one cassette into position.

6. The rig of claim 1, wherein the at least one cassette includes a guide channel to facilitate retraction and/or extension of the at least one tube relative to the at least one rotatable reel.

7. The rig of claim 1, wherein the at least one sensor comprises a camera.

8. The rig of claim 1, wherein the at least one sensor comprises a proximity sensor.

9. The rig of claim 1, wherein the at least one sensor comprises a contact sensor.

10. The rig of claim 1, further comprising at least one idler roller.

11. The rig of claim 1, wherein the at least one movable roller comprises at least two movable rollers opposing at least one idler roller.

12. The rig of claim 1, further comprising:
at least one processor configured to control at least one radius control system based at least partly on data received from the at least one sensor.

13. The rig of claim 1, further comprising at least one processor configured to control at least one motor to change a position of the at least one movable roller relative to the at least one tube based at least partly on a detected bend radius of the at least one tube.

14. The rig of claim 1, further comprising a radius control system is configured to adjust a bend radius of the at least one tube using the at least one movable roller based at least partly on data received from the at least one sensor and based at least partly from user input.

15. The rig of claim 1, wherein the at least one cassette includes a circumference wall that at least partially encloses the rotatable reel.

16. The rig of claim 15, wherein the at least one sensor is positioned on an inside surface of the circumference wall to detect bend radius information associated with the at least one tube.

17. The rig of claim 1, wherein the at least one cassette includes a sidewall that at least partially encloses the rotatable reel and wherein the at least one tube is extendable via an opening in the sidewall.

18. The rig of claim 1, wherein the at least one docking base includes at least one vertical protrusion that lockably engages one or more mating vertical recesses within the frame.

19. A cone penetration testing system, the system comprising:
a frame having one or more mounting receptacles;
a cassette that at least partially encloses at least one rotatable reel that rotates tubing inside the cassette, the cassette including one or more mounting protrusions configured to engage the one or more mounting receptacles of the frame;
at least one movable roller; and
at least one sensor,
wherein the at least one movable roller is configured to adjust a bend radius of tubing, based at least partly on data received from the at least one sensor.

* * * * *